US012691062B2

(12) United States Patent
Delplace et al.

(10) Patent No.: US 12,691,062 B2
(45) Date of Patent: Jul. 28, 2026

(54) DYNAMIC COVALENT HYDROGELS, PRECURSORS THEREOF AND USES THEREOF

(71) Applicants: Centre National de la Recherche Scientifique, Paris (FR); Institut National de la Santé et de la Recherche Médicale, Paris (FR); Nantes Universite, Nantes (FR)

(72) Inventors: Vianney Delplace, La Bernardiere (FR); Jérôme Guicheux, Sainte Luce sur Loire (FR); Catherine Le Visage, Nantes (FR); Arnaud Tessier, Orvault (FR)

(73) Assignees: Centre National de la Recherche Scientifique, Paris (FR); Institut National de la Sante et de la Recherche Medicale, Paris (FR); Nantes Universite, Nantes (FR)

( * ) Notice: Subject to any disclaimer, the term of this patent is extended or adjusted under 35 U.S.C. 154(b) by 824 days.

(21) Appl. No.: 17/910,478

(22) PCT Filed: Mar. 10, 2021

(86) PCT No.: PCT/EP2021/056065
§ 371 (c)(1),
(2) Date: Sep. 9, 2022

(87) PCT Pub. No.: WO2021/180795
PCT Pub. Date: Sep. 16, 2021

(65) Prior Publication Data

US 2023/0181462 A1 Jun. 15, 2023

(30) Foreign Application Priority Data

Mar. 10, 2020 (EP) .................................... 20162062

(51) Int. Cl.
*A61K 9/06* (2006.01)
*C08G 65/337* (2006.01)
*C08J 3/075* (2006.01)
*C08J 3/24* (2006.01)
*C08L 5/04* (2006.01)
*C08L 5/08* (2006.01)

(52) U.S. Cl.
CPC .............. *A61K 9/06* (2013.01); *C08G 65/337* (2013.01); *C08J 3/075* (2013.01); *C08J 3/24* (2013.01); *C08L 5/04* (2013.01); *C08L 5/08* (2013.01); *C08J 2305/04* (2013.01); *C08J 2305/08* (2013.01); *C08J 2371/02* (2013.01)

(58) Field of Classification Search
CPC ................................ A61K 9/06; C08G 65/337
See application file for complete search history.

(56) References Cited

U.S. PATENT DOCUMENTS

| | | | | |
|---|---|---|---|---|
| 2019/0169375 | A1* | 6/2019 | Auzely-Velty | C08K 5/1545 |
| 2020/0002441 | A1* | 1/2020 | Auzely-Velty | C08B 37/0072 |

FOREIGN PATENT DOCUMENTS

| | | | |
|---|---|---|---|
| WO | 2007/027493 A2 | | 3/2007 |
| WO | 2017/063749 A1 | | 4/2017 |
| WO | 2018/024793 A1 | | 2/2018 |
| WO | WO/2018/024793 | * | 2/2018 |

OTHER PUBLICATIONS

Marco-Dufort et al., "Design of moldable hydrogels for biomedical applications using dynamic covalent boronic esters," Materials Today Chemistry, 12: 16-33 (2019).
International Search Report issued in corresponding International Patent Application No. PCT/EP2021/056065 dated Jun. 9, 2021.
Written Opinion issued in corresponding International Patent Application No. PCT/EP2021/056065 dated Jun. 9, 2021.

* cited by examiner

*Primary Examiner* — Paul V Ward
(74) *Attorney, Agent, or Firm* — Morgan, Lewis & Bockius LLP

(57) ABSTRACT

The present invention provides crosslinking pairs of hydrogel precursor polymers, dynamic covalent hydrogels prepared from such crosslinking pairs of hydrogel precursors, pharmaceutical compositions comprising such precursors or hydrogels and uses thereof in a variety of applications.

23 Claims, 12 Drawing Sheets

Hyaluronic acid-based hydrogel

PEG-based hydrogel

A

B

DYNAMIC COVALENT HYDROGELS, PRECURSORS THEREOF AND USES THEREOF

RELATED PATENT APPLICATIONS

The present application is filed pursuant to 35 U.S.C. § 371 as a U.S. National Phase Application of International Patent Application No. PCT/EP2021/056065, which was filed on Mar. 10, 2021, claiming the benefit of priority to European Patent Application No. EP 20162062.2 filed on Mar. 10, 2020. The content of each of the aforementioned Patent Applications, is incorporated herein by reference in its entirety.

BACKGROUND OF THE INVENTION

Polymer networks are formed through physical or chemical crosslinking of functional monomeric or polymeric precursors. Physically crosslinked materials are held together by non-covalent, reversible interactions (De Greef et al., Chem. Rev., 2009, 109: 5687-5754). This generally yields shear-thinning (viscous flow upon increased shear) and self-healing (reformation of gel properties after shear cessation) materials, as the bonds can break and re-form in response to external stimuli, including mechanical load. However, the structures thus obtained are often unstable to small environmental perturbations and lack robustness. Chemically crosslinked networks, on the other hand, are held together by covalent bonds (Wichterle et al., Nature, 1960, 185: 117-118). This yields elastic gels with generally better mechanical properties than physical networks. However, the irreversibility of chemical crosslinks limits their use for applications that require shear-thinning and self-healing properties, such as 3D-printing and minimally invasive drug delivery.

Recent research has introduced a new class of soft matter based on dynamic covalent chemistry, which combines the benefits of both physically and chemically crosslinked materials (Kloxin et al., Chem. Soc. Rev., 2013, 42: 7161-7173). In this approach, reversible covalent bonds are formed in the network that can break and re-form on experimental timescales. Thus, these dynamic covalent networks rearrange because of the exchange of bonds, enabling stress relaxation and material flow. Crosslinking reactions that have been used in dynamic covalent network formation include transesterification, Diels-Alder cycloaddition, and boronic ester complexation. The reversible formation of boronic esters between boronic acids and cis-1,2 or cis-1,3 diols containing molecules has emerged as a safe and synthetically tractable dynamic covalent crosslinking motif for the design of stimuli-responsible biomedical materials. However, boronate ester complexes are generally favored at alkaline pH, the common diol coupling partners tend to produce relatively unstable condensation products and exhibit oxidative sensitivity.

Thus, there is still a need in the art for improved boronic acid/diol couples suitable to produce dynamic covalent hydrogels that can be used in controlled drug release, cell culture, tissue engineering, 3D-printing, etc.

SUMMARY OF THE INVENTION

The present Inventors have identified new boronic acid/diol couples for the formation of dynamic covalent hydrogels. Compared to systems known in the art, the present new boronic acid/diol couples exhibit several advantages. In particular, hydrogel formation may be carried out, in a single step, in physiological conditions of pH and temperature. Furthermore, the crosslinking reaction is essentially instantaneous. The hydrogels thus obtained are highly stable over time, self-healing and minimally swellable and have viscoelastic properties similar to those of living tissues. Due to their advantageous shear-thinning properties, the polymer compositions are injectable. In addition, the composition of the hydrogels can easily be varied in order to modulate their biodegradability and/or to mimic living tissues or environments.

Consequently, the present invention relates to a crosslinking pair of hydrogel precursor polymers comprising: (1) a first hydrogel precursor polymer consisting of a first polymer modified with a phenylboronic acid or a phenylboronic acid derivative, and (2) a second hydrogel precursor polymer consisting of a second a second polymer modified with glucamine.

In certain embodiments, the first polymer is grafted with phenylboronic acid or the phenylboronic acid derivative and the second polymer is grafted with glucamine.

In certain embodiments, the first and second polymers are independently selected natural polymers, semi-synthetic polymers, and synthetic polymers.

In certain embodiments, at least one of the first and second polymers is selected from biocompatible, biodegradable, hydrophilic natural polymers, semi-synthetic polymers, and synthetic polymers.

In certain embodiments, the first and second polymers are identical. In other embodiments, the first and second polymers are different.

In certain embodiments, the phenylboronic acid derivative is an ortho-, meta- or para-monosubstituted phenylboronic acid acid, a Wulff-type phenylboronic acid or a benzoxaborole. In certain preferred embodiments, the phenylboronic acid derivative is a Wulff-type phenylboronic acid.

In certain embodiments, the first hydrogel precursor polymer or the second hydrogel precursor polymer is directly or indirectly covalently linked to a bioorthogonal functional moiety or to a clickable moiety.

In certain embodiments, the crosslinking pair of hydrogel precursor polymers is such that the first hydrogel precursor polymer is in a first aqueous solution; and the second hydrogel precursor polymer is in a second aqueous solution, the first and second aqueous solutions being separate aqueous solutions. At least one of the first and second aqueous solutions may comprise a component selected from the group consisting of cells, bioactive agents, visualization agents, and any combination thereof.

The present invention also relates to a dynamic covalent hydrogel composed of a first hydrogel precursor polymer and a second hydrogel precursor polymer of a crosslinking pair as defined herein, wherein the first and second hydrogel precursors are crosslinked by dynamic covalent bonds. The dynamic covalent hydrogel may further comprise a component selected from the group consisting of cells, bioactive agents, visualization agents, and any combination thereof.

The present invention further relates to a pharmaceutical composition comprising a crosslinking pair of hydrogel precursor polymers as defined herein, or a dynamic covalent hydrogel as defined herein, and at least one pharmaceutically acceptable carrier our excipient.

In certain embodiments, the pharmaceutical composition is such that the first hydrogel precursor polymer and the second precursor hydrogel polymer are contained in a multi-barrel syringe, preferably a double-barrel syringe.

The present invention also relates to a crosslinking pair of hydrogel precursor polymers as defined herein, or a dynamic covalent hydrogel as defined herein, or a pharmaceutical composition as defined herein for use as a therapeutic agent.

The present invention also relates to a crosslinking pair of hydrogel precursor polymers as defined herein, or a dynamic covalent hydrogel as defined herein, or a pharmaceutical composition as defined herein for use as a therapeutic agent, for example in cell therapy, in tissue engineering, in regenerative medicine, in viscosupplementation, in delivery of cells and/or bioactive agents in vivo.

The present invention further relates to a kit comprising a crosslinking pair of hydrogel precursor polymers as defined herein, or a dynamic covalent hydrogel as defined herein, or a pharmaceutical composition as defined herein, and instructions to use the crosslinking pair, the dynamic covalent hydrogel or the pharmaceutical composition.

The present invention also relates to a method for preparing a dynamic covalent hydrogel comprising a step of mixing a first hydrogel precursor polymer and a second hydrogel precursor polymer of a crosslinking pair as defined herein to obtain a dynamic covalent hydrogel.

In certain embodiments, the method for preparing a dynamic covalent hydrogel is carried out under physiological conditions.

These and other objects, advantages and features of the present invention will become apparent to those of ordinary skill in the art having read the following detailed description of the preferred embodiments.

DETAILED DESCRIPTION OF CERTAIN PREFERRED EMBODIMENTS

Figure 1:
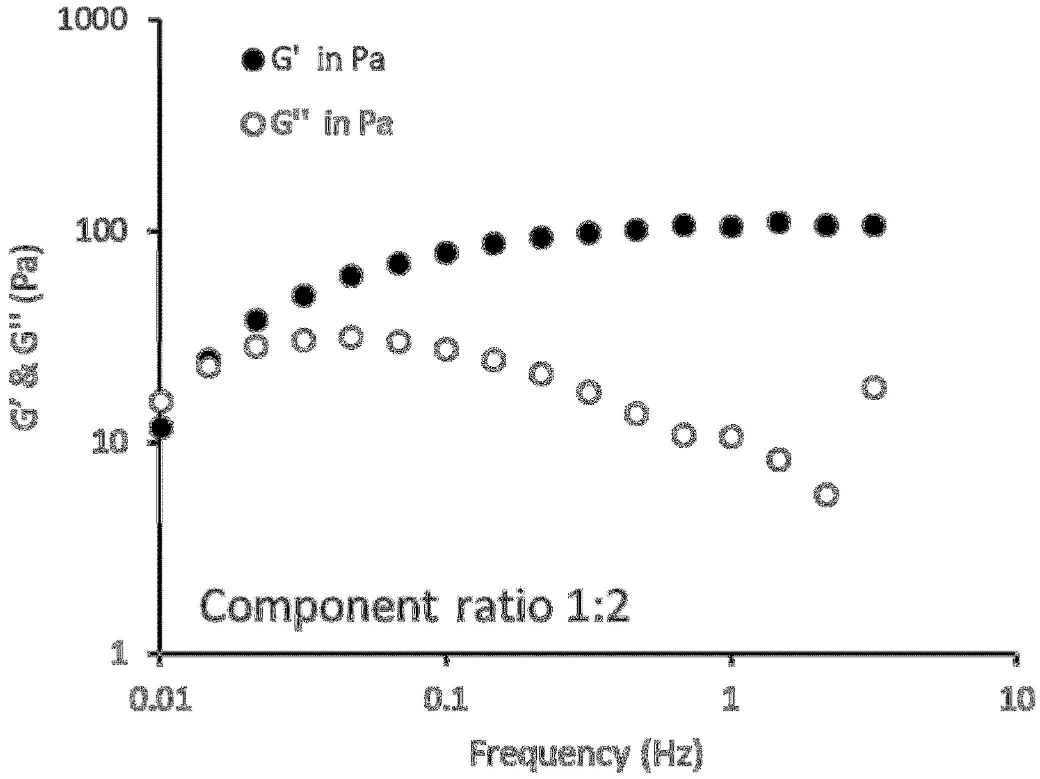
FIG. 1. Demonstration of the viscoelastic behavior of dynamic covalent hydrogels made of a mix of Wulff-PBA-modified and glucamine-modified polymer precursors. Mixing Wulff-PBA-modified hyaluronic acid and glucamine-modified hyaluronic acid in a 1:2 volume ratio, the storage modulus (G') and loss modulus (G") show the expected crossover when measured over a range of frequencies.
Figure 2:
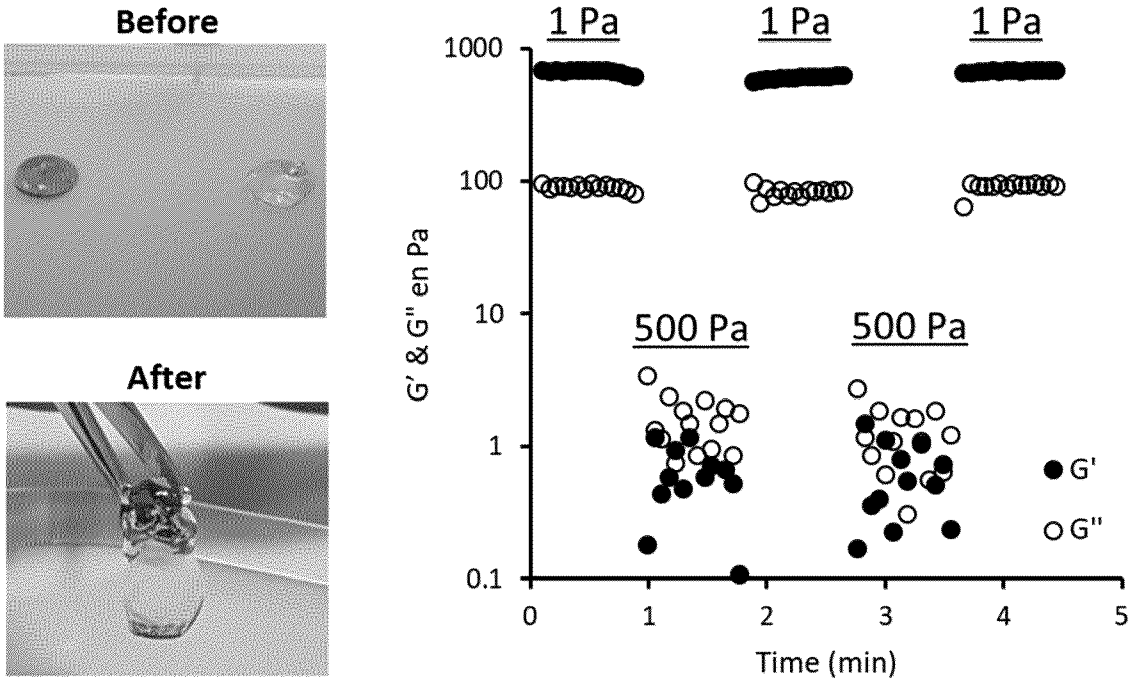
FIG. 2. Demonstration of the self-healing property of dynamic covalent hydrogels made of a mix of Wulff-PBA-modified and glucamine-modified polymer precursors. (A) Qualitatively, two hyaluronic acid (HA)-based dynamic covalent hydrogel form a single hydrogel within minutes, which can support its own weight. (B) Time sweep measurement on a typical HA-based dynamic covalent gel formulation (1% w/v) HA-Wulff-PBA mixed with HA-glucamine in a 1:1 volume ratio), at a constant frequency of 1 Hz, under alternated low (1 Pa) and high (500 Pa) stress, showing repeated disruption of the gel (G'<G") at high frequency and recovery of the initial mechanical properties (G'>G").

As mentioned above, the present invention provides hydrogel precursor polymers and dynamic covalent hydrogels, pharmaceutical compositions comprising such precursors or hydrogels and uses thereof in a variety of applications.

I—Pairs of Hydrogel Precursor Polymers

1. Hydrogel Precursor Polymers

The present invention provides crosslinking couples or pairs of hydrogel precursor polymers that are capable of crosslinking when mixed together. A crosslinking couple or pair of hydrogel precursor polymers according to the present invention is composed of a first hydrogel precursor polymer modified by a phenylboronic acid or a phenylboronic acid derivative and a second hydrogel precursor polymer modified by glucamine. The terms "couple", "pair", "crosslinking couple", and "crosslinking pair" are used herein interchangeably. They refer to an association or combination of two hydrogel precursor polymers, wherein the polymers are separated from each other, but which, when mixed, form a dynamic covalent hydrogel by crosslinking. In other words, the terms "couple", "pair", "crosslinking couple", and "crosslinking pair", as used herein, exclude mixture, blend, and synonymous thereof. As used herein, the term "hydrogel precursor polymer" refers to a polymer that can take part in a reaction to form a network of crosslinked molecules, e.g., a hydrogel. Thus, hydrogel precursor polymers in a pair as defined herein are the same materials as those that form a dynamic covalent hydrogel according to the invention, but they are not in contact with each other, and therefore, as a pair, cannot undergo crosslinking.

A. Polymers

In embodiments of the present invention where polymer precursors are to be used in biological, biomedical or medical applications, at least one of the first and second polymers is a biocompatible, biodegradable, hydrophilic polymer. The term "biocompatible", as used herein to characterize a polymer, refers to a polymer that is not significantly toxic to cells and/or living tissues, and that does not elicit an immunopathogenic response in healthy individuals. The term "biodegradable", as used herein to characterize a polymer, refers to a polymer that degrades through the action of living organisms, light, air, water or any combinations thereof. Preferably, a biodegradable polymer is a polymer which, inside the mammal body, undergoes over time disintegration into non-toxic molecules small enough to be metabolized or excreted under normal physiological conditions. As used herein, the "hydrophilic polymer" refers to a polymer (or copolymer) having groups with an affinity for water. The term "hydrophilic polymer" encompasses polymers absorbing greater than 0.5% of their weight of water within 24 hours, and greater than 4% at equilibrium, as determined by ASTM D570 testing.

The first and second hydrogel precursor polymers of a pair according to the present invention are independently selected from the group consisting of natural polymers, semi-synthetic polymers, and synthetic polymers. In embodiments of the present invention where polymer precursors are to be used in biological, biomedical or medical applications, the first and/or second hydrogel precursor polymers of a pair are biocompatible, biodegradable, hydrophilic polymers independently selected from the group consisting of natural polymers, semi-synthetic polymers, and synthetic polymers.

In certain embodiments, at least one of the first and second hydrogel precursor polymers is selected among natural polymers. The terms "natural polymers" and "biopolymers" are used herein interchangeably and refer to polymers that are naturally occurring (i.e., polymers that are found in nature but that may have been obtained using a method involving human intervention, e.g., isolation, purification, synthetic preparation, recombination preparation, and the like). In certain preferred embodiments, both the first and second hydrogel precursor polymers are natural polymers. Examples of natural polymers that are suitable for use in the present invention include naturally occurring polysaccharides, collagens, and gelatin.

As used herein, the term "polysaccharides" has its art understood meaning and refers to complex carbohydrates composed of 10 to up to several thousand monosaccharides arranged in chains and linked via glycosidic bonds. The most common monosaccharides that appear as parts of polysaccharides are glucose, fructose, galactose and mannose. The molecular weight of naturally occurring polysaccharides varies between hundreds to thousands of Daltons.

Exemplary polysaccharides include, but are not limited to, arabinans, fructans, fucans, galactans, galacturonans, glucans, mannans, xylans (such as, for example, inulin), levan, fucoidan, carrageenan, galatocarolose, pectic acid, pectins, amylose, pullulan, glycogen, amylopectin, cellulose, dextran, dextrin, dextrose, glycose, polyglucose, polydextrose, pustulan, chitosan, chitin, agarose, keratin, chondroitin sulfate, heparan sulfate, dermatan, hyaluronic acid, alginic acid (alginate), xanthan gum, and starch. Other examples of naturally occurring polysaccharides include other natural homopolymers or heteropolymers, such as those containing one or more of the following: aldoses, ketoses, erythrose, threose, ribose, arabinose, xylose, lyxose, allose, altrose, glucose, dextrose, mannose, gulose, idose, galactose, talose, erythrulose, ribulose, xylulose, psicose, fructose, sorbose, tagatose, mannitol, sorbitol, lactose, sucrose, trehalose, maltose, cellobiose, glycine, serine, threonine, cysteine, tyrosine, asparagine, glutamine, aspartic acid, glutamic acid, lysine, arginine, histidine, glucuronic acid, gluconic acid, glucaric acid, galacturonic acid, mannuronic acid, glucosamine, galactosamine, and neuraminic acid, and naturally occurring derivatives thereof.

In certain preferred embodiments, at least one of the first and second hydrogel precursor polymers is a naturally occurring polysaccharide selected from the group consisting of hyaluronic acid, alginate, cellulose, heparan sulfate, chondroitin sulfate, chitosan, and chitin.

In certain embodiments, at least one of the first and second hydrogel precursor polymers is a collagen. As used herein, the term "collagen" has its art understood meaning and refers to the most ubiquitous protein in the mammalian proteome. Collagen forms a large part of the extracellular matrix and connective tissue, offering strength and flexibility to tissues in the body. Any type of collagen may be used in the practice of the present invention. Thus, the collagen may be selected among type I collagen, type II collagen, type III collagen, type IV collagen, type VI collagen, and any combination thereof. Preferably, the collagen is derived from a human source or a porcine source.

In certain embodiments, at least one of the first and second hydrogel precursor polymers is gelatin. As used herein, the term "gelatin" has its art understood meaning and refers to an animal protein that is prepared from thermal denaturation of collagen isolated from animal skin and bones, with very dilute acid, or that is extracted from fish skins. Gelatin is a heterogeneous mixture of single or multi-stranded polypeptides, each with extended left-handed proline helix conformations and containing between 50 and 1000 amino acids. About half of the total amino acid content of gelatin are glycine residues (almost 1 in 3 residues, arranged every third residue), proline residues and 4-hydroxyproline residues.

In certain embodiments, at least one of the first and second hydrogel precursor polymers is selected among modified biopolymers. The terms "modified biopolymers" and "semi-synthetic polymers" are used herein interchangeably and refer to naturally occurring polymers that have been chemically modified. Examples of modified biopolymers that are suitable for use in the present invention include derivatized celluloses (such as carboxymethylcellulose, hydroxymethylcellulose, hydroxy-propylcellulose, methylcellulose and methoxy-cellulose); derivatized hyaluronic acid (such as amine-modified hyaluronic acids and esterified hyaluronic acids); and derivatized collagens (such as amino-modified collagens and esterified collagens).

In certain preferred embodiments, at least one of the first and second hydrogel precursor polymers is a biocompatible, biodegradable, hydrophilic semi-synthetic polymer selected from the group consisting of carboxymethylcellulose, hydroxymethylcellulose, hydroxypropyl-cellulose, methylcellulose and methoxycellulose.

In certain embodiments, at least one of the first and second hydrogel precursor polymers is selected synthetic polymers. As used herein, the term "synthetic polymer" refers to a polymer that is neither a naturally occurring polymer nor a semi-synthetic polymer. Examples of synthetic polymers suitable for use in the context of the present invention include, but are not limited to, poly(acrylic acid) and its derivatives, poly(ethylene glycol) and its copolymers, poly(vinyl alcohol), poly(2-hydroxy-ethyl methacrylate, polyphosphazenes, polycaprolactones, or co-polymers thereof. Other examples include polyacrylate derivatives, polymethacrylate derivatives (e.g., PEGMAs), polyisoprene, polyamides, synthetic polypeptides (e.g., PBLG), polylactic acid (PLA), poly(lactic-co-glycolic acid) (PLGA), and polycaprolactone (PCL).

One skilled in the art will understand that the list of polymers provided above is non-exhaustive and may be expended to other similar polymers.

In the context of the present invention, a hydrogel precursor polymer may have any suitable molecular weight. For example, the polymer may have a molecular weight of from about 5 000 g/mol to about 3 000 000 g/mol, preferably from about 10 000 g/mol to about 700 000 g/mol. The terms "approximately" and "about", as used in the present document, in reference to a number, generally include numbers that fall within a range of 10% in either direction of the number (greater than or less than the number) unless otherwise stated or otherwise evidenced from the context (except where such number would exceed 100% of a possible value).

B. Phenylboronic Acid and Phenylboronic Acid Derivatives

The first hydrogel precursor polymer according to the present invention is modified by phenylboronic acid or a phenylboronic acid derivative. The term "modified by phenylboronic acid or a phenylboronic acid derivative", wherein used herein to characterize a polymer, refers to a polymer that is grafted with phenylboronic acid or phenylboronic acid derivative (i.e., a polymer that is covalently linked to phenylboronic acid or a phenylboronic acid derivative such that the polymer is functionalized with phenylboronic acid or a phenylboronic acid derivative). Phenylboronic acid (or a phenylboronic acid derivative) molecule may be covalently attached to the polymer via its ortho, meta or para position (relative to the boronic acid group).

The term "phenylboronic acid", as used herein, refers to the molecule having the chemical formula (I) below and abbreviated as $PhB(OH)_2$ or PBA.

(I)

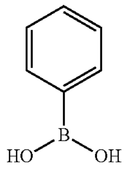

As used herein, the term "phenylboronic acid derivative" refers to a derivative of phenylboronic acid selected from the group consisting of ortho-, meta- or para-monosubstituted phenylboronic acid acids, Wulff-type phenylboronic acids and benzoxaboroles.

As used herein, the term "substituted" indicates that the particular group or compound being described has at least one hydrogen atom replaced by a non-hydrogen substituent. In the context of the present invention, the phenylboronic acid molecule is substituted to the extent that such substitution makes sense chemically. Examples of suitable substituents include, but are not limited to, alkyl, nitro ($—NO_2$), sulfo ($—SO_4—$), cyano (—CN), halogen (F, Br, Cl, or I), amine (—NRR', where each of R and R' is independently H or an alkyl), hydroxyl (—OH), sulfydryl (—SH), alcoxy (—OR, where R is an alkyl), alkylthio (—SR, where R is an alkyl), alkylsulfo ($—O—SO_2—O—R$, wherein R an alkyl), aldehyde (—CHO), ketone (—CO—R, where R is an alkyl), ester (—COO—R or —OCO—R, where R is an alkyl), amide (—CO—NRR', where each of R and R' is independently H or an alkyl), carboxylic acid (—COOH or —COOM, where M is a suitable cation, such as sodium or potassium), and sulfonic acid ($—SO_3H$ ou $—R—SO_3H$, where R is an alkyl) groups. One skilled in the art will know how to select a substituted phenylboronic acid such that the substituent is incompatible with grafting of the PBA onto polymers.

As used herein the term "alkyl" refers to a monovalent straight or branched chain group derived from an unsaturated hydrocarbon of one to ten carbon atoms (C1-C10 alkyl), for example of one to eight carbon atoms (C1-C8 alkyl) or from one to five carbon atoms (C1-C5 alkyl). Representative saturated straight chain alkyls include methyl, ethyl, n-propyl, n-butyl, n-pentyl, n-hexyl, n-heptyl, n-octyl, n-nonyl and n-decyl; while saturated branched alkyls include isopropyl, sec-butyl, isobutyl, tert-butyl, isopentyl, and the like. An alkyl group may optionally be substituted. For example, an alkyl group may be substituted by at least one substituent selected from the group consisting of nitro, sulfo, cyano, halogen, amine, hydroxyl, aldehyde, ketone, ester, amide, carboxylic acid and sulfonic acid groups.

Specific examples of monosubstituted phenylboronic acids include, but are not limited to, 2- (or 3- or 4-)bromophenylboronic acid, 2- (or 3- or 4-)chlorophenylboronic acid, 2- (or 3- or 4-)fluorophenylboronic acid, 2- (or 3- or 4-)iodophenylboronic acid, 2- (or 3- or 4-)nitrophenylboronic acid, 2- (or 3- or 4-)mercaptophenylboronic acid, 2- (or 3- or 4-)hydroxyphenylboronic acid, 3-sulfamoylbenzeneboronic acid, 2- (or 3- or 4-)aminophenylboronic acid, 2- (or 3- or 4-)(trifluoromethyl)phenylboronic acid, 2- (or 3- or 4-)(trifluoromethoxy)phenylboronic acid, 2- (or 3- or 4-)cyanophenylboronic acid, 2- (3- or 4-)formylphenylboronic acid, 2- (or 3- or 4-)carboxyphenylboronic acid, 2- (or 3- or 4-) (bromomethyl)phenylboronic acid, 2- (or 3- or 4-)aminocarbonylphenylboronic acid, o-tolylborinic acid, m-tolylboronic acid, p-tolylboronic acid, 2- (or 3- or 4-) (methylthio)phenylboronic acid, 2-methoxy (or 3- or 4-)phenylboronic acid, (or 3- or 4-) (hydroxylmethyl)phenylboronic acid, 2- (or 3- or 4-)methylsulfinylphenylboronic acid, 2- (or 3- or 4-)methylsulfonylphenylboronic acid, (2- (or 3- or 4-) [(methylamino)sulfonyl]-phenyl)boronic acid, (2- (or 3- or 4-) [(methylsulfonyl)-amino]phenyl)boronic acid, (2- (or 3- or 4-)amino-methylphenyl)boronic acid, 3-(2,2,2-trifluoroethoxy)phenylboronic acid, 4-(cyanomethyl)benzeneboronic acid, 4-cyano-methoxyphenylboronic acid, 4-(2-nitrovinyl)phenylboronic acid, 2- (or 3- or 4-)vinylphenylboronic acid, 2- (or 3- or 4-)acetylphenylboronic acid, 2- (or 3- or 4-) methoxycarbonylphenylboronic acid, 2- (or 3- or 4-)acetamidophenylboronic acid, 2-(or 3- or 4-)ethylphenylboronic acid, 2- (or 3- or 4-)ethoxyphenylboronic acid, 3-(ethylthio)phenylboronic acid, 3-ethylsulfinylphenylboronic acid, 4-ethyl sulfinyl-phenylboronic acid, 3 (N,N-dimethylamino)phenylboronic acid, 4-(methyl sulfonyl-aminomethylphenyl)boronic acid, 2- (or 3- or 4-)ethoxycarbonylphenylboronic acid, (4-acetamidomethylphenyl) boronic acid, 2-(dimethylaminocarbonyl)benzeneboronic acid, 4-(dimethylcarbamoyl)-phenylboronic acid, 2- (or 3- or 4-)isopropylphenylboronic acid, 4-propylphenylboronic acid, 3-propoxyphenylboronic acid, [3-(3-hydroxyl-propyl) phenyl]boronic acid, 4-(3-hydroxypropyl)benzeneboronic acid, 4-isopropoxyl-phenylboronic acid, 4-propoxyl-phenylboronic acid, 3-tert-butylphenylboronic acid, 4-tert-butylphenylboronic acid, 4-butylphenylboronic acid, 2-(3- or 4-)butoxy-phenylboronic acid, 2-isobutoxy-phenylboronic acid, 3-isobutoxyphenylboronic acid, 4-(dimethylamino)phenylboronic acid, 3-(isobutylaminocarbonyl)phenylboronic acid, and 4-(isobutylaminocarbonyl) phenylboronic acid.

The term "Wulff-type phenylboronic acids", as used herein, refers to phenylboronic acid derivatives that contain intermolecular tetracoordinated B—N (chemical formula (II)) bonds, which facilitate the formation of tetragonal boronate anion (sp3). The sp3 hybridization status remains stable even under neutral or moderately acidic conditions, facilitating boronate esterification with cis-diols.

(II)

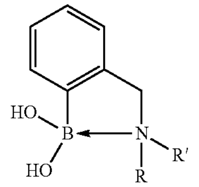

Wulff-type phenylboronic acids have been described (Wulff et al., Pure Appl. Chem., 1982, 54: 2093-2102; Wulff et al., Angew Chem., Int. Ed. Engl., 1984, 23: 741-742). Examples of suitable Wulff-type phenylboronic acids include, but are not limited to, 2-((dimethylamino)methyl)phenylboronic acid (DAPBA). Wulff-type boronic acids, similar to the structure of 2-dimethylaminomethylphenylboronic acid (DAPBA), are of great interest in biomedical applications (Cromwell et al., J. Am. Chem. Soc., 2015, 137: 6492-6495; Piest et al., Soft Matter, 2011, 7: 11111; Li et al., Chem. Commun., 2011, 47: 8169; Kim et al., J. Am. Chem. Soc., 2009, 131: 13908-13909).

In certain preferred embodiments, the Wulff-type phenylboronic acid has formula (II), wherein R and R' are independently selected from hydrogen, substituted or unsubstituted $C_1$-$C_{20}$ alkyl, substituted or unsubstituted $C_1$-$C_{10}$ alkenyl, substituted or unsubstituted $C_1$-$C_{10}$ alkynyl, acyl (—C(═O)$R_1$, wherein $R_1$ is a substituted or unsubstituted $C_1$-$C_{20}$ alkyl group) and carboxy (—C(═O)O$R_1$, wherein $R_1$ is a substituted or unsubstituted $C_1$-$C_{20}$ alkyl group). Alkyl, alkenyl and alkynyl groups can be substituted with one or more substituents, such as for example substituents selected from halogen (F, Br, I, C1), hydroxy (—OH), amino (—N $R_2R_3$, wherein $R_2$ and $R_3$ are independently selected from hydrogen and substituted or unsubstituted $C_1$-$C_{20}$ alkyl), alkoxy (—OR', wherein $R_1$ is a substituted or unsubstituted $C_1$-$C_{20}$ alkyl group), carboxy (—C(═O)O$R_1$, wherein $R_1$ is a substituted or unsubstituted $C_1$-$C_{20}$ alkyl group), amido (—N$R_2$C(═O)$R_3$ or —C(═O)N$R_2$R3, wherein $R_2$ and $R_3$ are independently selected from hydrogen and substituted or unsubstituted $C_1$-$C_{20}$ alkyl), nitro (—$NO_2$), oxo (═O), and cyano (—CN).

The Wulff-type phenylboronic acid of formula (II) may also be such that one of R and R' is a linking moiety or spacer comprising at the free (non-attached end) a reactive group capable of attaching to, or reacting, with the polymer onto which the Wulff-type phenylboronic acid is destined to be grafted. The terms "linking moiety", "linker" and "spacer" are used herein interchangeably and refer to a moiety having a backbone of at least 8 atoms in length, for example more than 10, more than 20, more than 30, more than 35, more than 40, or more than 50 atoms in length. The linker may be linear, branched, cyclic or a single atom. In certain cases, the linker is substituted with a sulfur, nitrogen or oxygen heteroatom. The bonds between backbone atoms may be saturated or unsaturated. The linker may include one or more substituent groups.

In certain embodiments, the phenyl group of the Wulff-type phenylboronic acid of formula (II) is substituted (see definition above) by at least one substituent. In certain embodiments, a substituent is selected such that it allows the grafting of the Wulff-type phenylboronic acid onto the first polymer. Alternatively, a substituent on the phenyl group is a linking moiety terminated with a functional group that can be used to graft the Wulff-type phenylboronic acid onto the first polymer.

The phenyl group in the Wulff-type phenylboronic acid of formula (II) is also envisioned to be replaced with a heteroaryl group. As used herein, the term "heteroaryl" refers to a monocyclic or bicyclic radical of 5 to 10 ring atoms having at least one aromatic ring containing one, two, or three ring heteroatoms selected from N, O, and S, the remaining ring atoms being carbon atoms, with the understanding that the attachment point of the heteroaryl radical will be on an aromatic ring. In certain embodiments, the heteroaryl is a heterophenyl group. As used herein, the term "heterophenyl" refers to a phenyl group in which at least one carbon atom is substituted by a heteroatom selected from N, O and S.

The term "benzoxaboroles", as used herein, refers to cyclic boronic acid hemiesters, and in particular to bicyclic organic heterocycles having chemical formula (III).

(III)

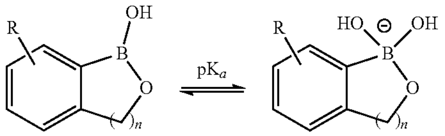

Such compounds with intramolecular B—O coordination (Berubé et al., J. Org. Chem., 2008, 73: 6471-6479; Dowlut et al., J. Am. Chem. Soc., 2006, 128: 4226-4227) have been described.

In certain preferred embodiments, the benzoxaborole has formula (III), wherein n is an integer equal to 1, 2, 3, 4, 5, 6, 7 or 8 and wherein the phenyl ring is substituted (see definition above) by at least one substituent. Thus, in formula (III), R is one or more (i.e., 1, 2, 3 or 4) substituents. At least one of the substituents is selected such that it allows the grafting of the benzoxaborole onto the first polymer. Alternatively, a substituent on the phenyl group of formula (III) is a linking moiety terminated with a functional group that can be used to graft the benzoxaborole onto the first polymer. The phenyl group in the benzoxaborole of formula (III) is also envisioned to be replaced with a heteroaryl group, for example a heterophenyl group.

C. Glucamine

The second hydrogel precursor polymer according to the present invention is modified by glucamine. As used herein, the term "modified by glucamine" refers to a polymer that is grafted with glucamine (i.e., a polymer that is covalently linked to glucamine such that the polymer is functionalized with glucamine). As used herein, the term "glucamine" refers to the molecule having the chemical formula (IV) below. Glucamine is also known as D-glucamine, and its IUPAC name is (2R,3R,4R,5S)-6-aminohexane-1,2,3,4,5-pentol.

(IV)

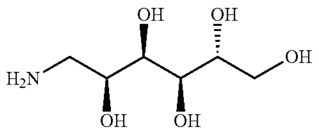

2. Preparation of Hydrogel Precursors

The first hydrogel precursor polymer modified by a phenylboronic acid or a phenylboronic acid derivative and the second hydrogel precursor polymer modified by glucamine may be prepared using any suitable method known in the art or using a procedure adapted from methods known in the art. Methods for grafting phenylboronic acids on polymers are known in the art (Ryu et al., Curr. Med. Chem., 2018, doi: 10.2174/0929867325666181008144443, Brooks and Sumerlin, Chem. Rev., 2016, 3: 1375-1397; Guan and Zhang, Chem. Soc. Rev., 2013, 42: 8106-8121). Similarly, methods for grafting diols on polymers are known in the art (Tarus et al., Macromol. Rapid Commun., 2014, 35: 2089-2095; Figueiredo et al., Tang et al., Adv. Sci., 2018, 5(9): 1800638; Yesilyurt et al., Adv. Mater., 2015, 28(1): 86-91).

In certain embodiments, the grafting may be carried out using a method described in the Examples section below.

The reaction to obtain the second hydrogel precursor polymer modified by glucamine allows the diol substitution level to be varied, in a controlled manner, in a wide range (e.g., anywhere from about 0.5% to about 100%, for example from about 1% to about 99%). Indeed, since glucamine is completely soluble, it does not render the polymer more hydrophobic. Thus, there is no limitation in the molar ratio between the polymer and glucamine.

The hydrogel precursor polymers may be purified using any method known in the art. Examples of suitable methods of purification include, but are not limited to, washing, filtration, precipitation, decantation, centrifugation, distillation, and the like, or any combination thereof.

If desired, after preparation, at least one of the first and second hydrogel precursors is placed into solution prior to use or to storage. Preferred solutions are aqueous solutions having a pH between about 6 and about 8. In certain preferred embodiments, the aqueous solutions are physiologically compatible solutions, such as buffered isotonic saline (see "formulations" below).

Alternatively, if desired, after preparation, at least one of the first and second hydrogel precursors is dried under vacuum (for example freeze-dried or lyophilized) into a substantially anhydrous form or a powder. Thereafter, the powder can be rehydrated before use.

If desired, after preparation, a hydrogel precursor polymer may be sterilized. Sterilization may be carried out using any of a wide variety of sterilization techniques known in the art, for example by filtration through a bacteria-retaining filter, by gamma irradiation, by electron-beam irradiation, or by incorporating sterilizing agents in the form of sterile solid compositions which can be dissolved or dispersed in sterile water or other sterile injectable medium prior to use.

The hydrogel precursor polymers may be stored under appropriate conditions, either in a liquid form or a solid form. Appropriate storage conditions for polymers are known in the art. For example, lyophilized/anhydrous hydrogel precursor polymers may be stored in a sealed container at −20° C. The hydrogel precursor polymers may be stored under appropriate conditions for a period of a few days, a few weeks, or a few months.

In certain embodiments, each of the first and second hydrogel precursors is placed in a recipient, for example in a vial, a flask or other hermetic container. When hydrogel precursor solutions are used, each solution may be placed in a syringe, for example a double-barrel syringe or any other suitable syringe system in which the first and second hydrogel precursor polymers are physically separated prior to simultaneous extrusion and concomitant mixing and co-injection of the mixed first and second hydrogel precursors through a needle (cannula) in the body of a subject (see "kits" below).

3. Additional Components

Depending on the intended use of a crosslinking pair of hydrogel precursors, at least one of the first and second hydrogel precursor polymers or hydrogel precursor solutions may comprise cells, a bioactive agent, a visualization agent, or a combination thereof. Examples of such cells, bioactive agents and visualization agents are provided below (see Pharmaceutical Compositions and Kits below).

The bioactive agent or visualization agent may be attached to at least one of the hydrogel precursor polymers, either covalently or ionically. Alternatively, the bioactive agent or visualization agent may be mixed with at least one of the hydrogel precursor polymers or hydrogel precursor polymer solutions.

With the goal of widening the scope of biomedical applications of the dynamic covalent hydrogels of the present invention, the first hydrogel precursor polymer or the second hydrogel precursor polymer of a crosslinking pair of hydrogel precursors may be modified to be covalently linked to a reactive chemical moiety, in particular to a bioorthogonal functional moiety or to a clickable moiety. The presence of a bioorthogonal functional moiety or of a clickable moiety may be used to tune the physicochemical properties of the hydrogel, in time and space. For example, it can be used to stabilize and/or mechanically reinforce a bioprinted construct post-printing. Alternatively, or additionally, the presence of a bioorthogonal functional moiety or of a clickable moiety may be used to facilitate post-gelation immobilization of molecules of interest (e.g., peptides, growth factors, drugs, fluorophores, and the like), the development of evolutive 3D culture system with cell-material interactions adjusted in time and space, etc. . . . .

Thus, in certain embodiments, the first hydrogel precursor polymer or the second hydrogel precursor polymer of a crosslinking pair of hydrogel precursors is directly or indirectly covalently linked to a bioorthogonal functional moiety or to a clickable moiety. As used herein, the term "bioorthogonal functional moiety or clickable moiety" refers to a reactive chemical group that can participate in a "bioorthogonal chemical reaction or click chemical reaction" and that belongs to a pair of chemical reaction partners. Bioorthogonal chemical reactions and click chemical reactions are conjugation reactions known in the art. The term "bioorthogonal chemical reactions" more particularly refers to reactions that make use of chemical reaction pairs that (1) do not naturally occur in biological systems; (2) do not cross-react with functional groups that are present in biology; and (3) do not require cytotoxic catalysts or produce cytotoxic byproducts. Examples of bioorthogonal chemical reactions include the Staudinger ligation which utilizes two reaction partners, an azide and a functionalized triarylphosphine, to form a stable amide bond; the strain-promoted azide-alkyne cycloaddition (SPAAC or copper-free click chemistry), which makes use of azides and strained cyclooctynes to yield stable triazole linkages via 1,3-dipolar cycloaddition; a 1,3-cycloaddition between a nitrone and a cyclooctyne or between norbornene and a nitrile oxide (norbornene cycloaddition); oxime/hydrazine formation from aldehydes and ketones; the tetrazine ligation, which involves an alkene (e.g., trans-cyclooctene, norbornene) and an s-tetrazine in an inverse-demand Diels Alder reaction followed by a retro-Diels Alder reaction to eliminate nitrogen gas, the isocyanide-based click reaction, and the quadricyclane ligation. The terms "click reactions", "click chemical reactions" and "click chemistry" are used herein interchangeably. They more particularly refer to reactions that are "modular, wide in scope, give very high yields, generate only inoffensive byproducts that can be removed by nonchromatographic methods, and are stereospecific" (Kolb et al., Angew. Chem., Int. Ed., 2001, 40: 2004-2021). Such reactions should require "simple reaction conditions (ideally, the process should be insensitive to oxygen and water), readily available starting materials and reagents, the use of no solvent or a solvent that is benign (such as water) or easily removed, and simple product isolation" (Kolb et al., Angew Chem., Int. Ed., 2001, 40: 2004-2021). Therefore, the term "click chemistry" encompasses a broader range of reactions that are robust, but not necessarily free of off-target effects, in biological contexts, even though some click reactions are bioorthogonal chemical reactions. Click reactions include 1,4-conjugate additions (i.e., thiol-vinyl sulfone and thiol-maleimide reactions), aldehyde-nucleophile reactions (hydrazone and oxime ligations), Diels-Alder reactions, and photoactivated thiol-ene coupling.

A bioorthogonal functional moiety to be used in the practice of the present invention belongs to a pair of bioorthogonal partners, while a clickable moiety belongs to a pair of click reaction partners. A bioorthogonal functional moiety or a clickable moiety may be any suitable chemical group that belongs to a pair of bioorthogonal partners or to a pair of click reaction partners. Representative pairs of such reaction partners are described, for example, in "Bioconjugate Techniques", Greg T. Hermanson, 1996 and Patterson et al., ACS Chemical Biology, 2014, 9: 592-605; Spicer et al., Nature Communications, 2014, 5: 4740; Madl and Heilshorn, Advanced Functional Materials, 2018, 28(11): 1706046. Thus, for example, a bioorthogonal functional moiety or a clickable moiety may be selected from the group consisting of cyclooctenes; trans-cyclooctenes; tetrazines; azides; alkynes, including strained alkynes, e.g., cyclooctynes or cyclooctyne derivatives; amines; activated esters; isocyanates; isothiocyanates; thiols; aldehydes; amides; norbornenes; vinyl derivatives including acrylates, methacrylates and the like; phosphines such as triarylphosphines; nitrones; quadricyclanes; maleimides; hydrazones and the like. Other bioorthogonal functional moieties and clickable moieties may be used.

The bioorthogonal functional moiety or the clickable moiety may be directly or indirectly (e.g., via a linker) covalently attached to the first hydrogel precursor polymer or the second hydrogel precursor polymer of a crosslinking pair of hydrogel precursors. It may be attached to the first polymer, to the phenylboronic acid or phenylboronic acid derivative, to the second polymer, or to the glucamine. In certain preferred embodiments, the bioorthogonal functional moiety or the clickable moiety is directly or indirectly (e.g., via a linker) covalently attached to the first polymer or to the second polymer. As will be recognized by those skilled in the art, more than one bioorthogonal functional moiety or clickable moiety may be attached to the first or second hydrogel precursor.

In certain embodiments, conjugation employing a bioorthogonal or click reaction typically involves a two-step strategy: first, the introduction of a bioorthogonal functional moiety or of a click moiety into the first hydrogel precursor polymer or into the second hydrogel precursor polymer of a crosslinking pair of hydrogel precursors followed, after formation of the dynamic covalent hydrogel, by introduction of the desired molecule or biomolecule via bioorthogonal or click conjugation.

In other embodiments, conjugation employing a bioorthogonal or click reaction may be used for the synthesis of double-lattice gels (i.e., mixture of 4 polymers forming networks 2 to 2) or in co-crosslinking (mixture of 3 polymers with a polymer participating in 2 networks). Co-crosslinking may be performed in one step or two steps.

II—Dynamic Covalent Hydrogels

The present invention also provides dynamic covalent hydrogels composed of the two hydrogel precursor polymers of a crosslinking pair described herein. A used herein, the term "hydrogel" has its art understood meaning and refers to a three-dimensional polymeric structure that is insoluble in water or other aqueous media, but which is capable of absorbing and retaining water to form a stable, often soft and pliable, structure. In embodiments of the present invention wherein a hydrogel is to be used in biological, biomedical or medical applications, a hydrogel may be composed of at least one biocompatible, biodegradable, hydrophilic polymer. Crosslinked hydrogels can be considered as solids because they do not flow or deform without application of shear stress. However, crosslinked hydrogels with certain formulations could be distorted under the effect of gravity. "Hydrogel" may be interchangeable with "hydrogel scaffold" or "scaffold" or "viscoelastic material". A hydrogel according to the present invention may be formed in vitro. Alternatively, a hydrogel may be formed in situ, i.e., may be a hydrogel whose formation occurs at a tissue site in a living animal or human body (see below). A hydrogel according to the present invention can further enclose or comprise any number of cells, biomolecules, and/or bioactive agents (see below).

1. Dynamic Covalent Hydrogels

A hydrogel according to the present invention is composed of a first hydrogel precursor polymer modified with phenylboronic acid or a phyenylboronic acid derivative as described above, and a second hydrogel precursor polymer modified with glucamine as described above, wherein the first and the second polymers are crosslinked by dynamic covalent bonds.

As used herein the term "dynamic covalent bond" refers to a covalent bond that can reversibly form and dissociate. For example, the constitution of dynamic systems can respond to changes in chemical environment (complexing entities, etc) or physical conditions (temperature, mechanical stress, electric field, irradiation, etc). In the context of the present invention, the first and the second hydrogel precursor polymers are crosslinked by dynamic covalent bonds formed between a boronic acid function on the first polymer and a diol function on the second polymer. Boronic acids have the ability to form reversible covalent bonds with 1,2- and 1,3-diols (Brighid Pappin et al., Boron-Carbohydrate Interactions) leading to the formation of boronate esters. Thus, in a hydrogel according to the present invention, the first and second hydrogel precursor polymers are crosslinked by dynamic covalent boronate ester bonds.

A hydrogel according to the invention is a "dynamic covalent hydrogel". The dynamic properties of the crosslinks by boronic ester bonds provides hydrogels which exhibit viscous flow under shear stress (shear-thinning) and rapid recovery when the applied stress is relaxed (self-healing). As used herein, the term "self-healing" refers to the spontaneous formation of new bonds when old bonds are broken within a material. Thus, a self-healing hydrogel according to the present invention autonomously repairs external stress damage and substantially recovers its original modulus and strength. The stress is typically applied via physical force and/or pressure. "Self-healing" is thus a process in which a hydrogel having reduced resistance to flow when subjected to external stress, regains some, or all, of its rigidity and strength after the external stress is removed. As used herein, the term "shear-thinning" refers to the effect where a hydrogel's viscosity (the measure of a fluid's resistance to flow) decreases with an increasing rate of shearing or increased shear stress. Shear-thinning and self-healing hydrogels exhibit many unique and useful properties, including externally tunable strength, moldability, and low-energy synthesis/processing. In certain embodiments, upon removal of the mechanical shear force, the original hydrogel recovers within 30 minutes, preferably within about 20 minutes, or about 10 minutes, or about 5 minutes or about 1 minute, or within about 60 seconds, about 45 seconds, about 30 seconds, about 15 seconds, about 10 seconds, about 5 seconds or about 1 second. In the case of the hydrogels prepared by the present Inventors, recovery was in the order of seconds.

Preferably, a dynamic covalent hydrogel according to the present invention is biocompatible. The terms "biocompatible" and "medically acceptable" are used herein interchangeably. They refer to a material that is not significantly toxic to cells and/or living tissues. When used in medical applications, hydrogels are considered biocompatible if, after being placed in the physiological environment there is minimal inflammatory reaction, no evidence of anaphylactic reaction, and minimal unwanted cellular growth on the biomaterial surface. Upon implantation in a host mammal, a biocompatible hydrogel does not elicit a host response sufficient to detrimentally affect the function of the hydrogel; such host responses include formation of fibrotic structures on or around the hydrogel, immunological rejection of the hydrogel, or release of toxic or pyrogenic compounds from the hydrogel into the surrounding host tissue and/or fluid.

Preferably, a dynamic covalent hydrogel according to the present invention is biodegradable. As used herein, the term "biodegradable" refers to the predictable disintegration of the hydrogel into molecules small enough to be metabolized or excreted under normal physiological conditions.

A dynamic covalent hydrogel according to the invention that is prepared in vitro (or ex vivo) may be of any desired shape (geometry) and dimensions (size). As will be understood by one skilled in the art, shape and dimensions will generally be dictated by the intended use of the hydrogel (e.g., 3D-cell culture, tissue engineering, etc.). Shaping and sizing can include custom shaping and sizing to match an implantable device to a specific treatment site in a specific patient, as determined by imaging or other techniques known to those in the art.

In certain embodiments, a hydrogel may be formed as microparticles or nanoparticles having a size comprised between about 50 nm and about 1000 nm, preferably between about 100 nm and about 500 nm. These nanoparticles are suitable for administration by injection. However, due to the shear-thinning/shear-healing properties of the hydrogels described herein, the use of microparticles or nanoparticles is not required for easy injectability.

2. Preparation of Dynamic Covalent Hydrogels

A dynamic covalent hydrogel according to the present invention is formed by crosslinking between a first hydrogel precursor polymer modified by phenylboronic acid or a phenylboronic acid derivative and a second hydrogel precursor polymer modified by glucamine. The reaction takes place in a single step of mixing the first and second hydrogel precursor polymers, each polymer being contained in a solution.

The crosslinking reaction may take place in vitro (including ex vivo, i.e., in vitro before administration to a subject). Alternatively, a hydrogel may be formed in situ (e.g., directly at a given site in a living animal or human body). In this case, hydrogel formation is initiated by mixing the two hydrogel precursor polymers at the site of injection.

The crosslinking reaction is performed in the absence of any catalyst under physiological conditions. As used herein, the term "physiological conditions" refers to an artificial environment which mimics a natural environment that is compatible with living cells, e.g., predominantly aqueous conditions of temperature, pH, osmotic pressure, osmolality, oxidation, and electrolyte concentration that are compatible with living cells and/or that are optionally considered within a normal range at the site of administration or of action in a subject. When the crosslinking reaction takes place in vitro (or ex vivo), physiological conditions include aqueous solutions having a pH ranging from about 6 to about 8, preferably about 7.2-7.4, and at a temperature comprised between about 4° C. to about 42° C. When the crosslinking reaction takes place in situ, the two hydrogel precursor polymers are placed in buffered aqueous solutions having a pH ranging from approximately 7.4 (for example between about 7 and 7.6), and a temperature from about 30° C. to about 42° C., preferably about 37° C.

The formation of a dynamic network at physiological pH is unusual compared to other boronate-cis-diol complexes, which can only stably exist at alkaline pH (Springsteen et al., Tetrahedron, 2002, 58: 5291-5300; Peters, Coordination Chemistry Reviews, 2014, 268: 1-22).

In the reaction mixture, the molar ratio between the first hydrogel precursor polymer and the second polymer precursor polymer may be of any value that yields a dynamic covalent hydrogel. In certain embodiments, the molar ratio between the first hydrogel precursor polymer and the second polymer precursor polymer is comprised between about 1:10 and about 10:1, for example between about 1:8 and about 8:1, or between about 1:6 and about 6:1, or between about 1:4 and about 4:1, or yet between about 1:2 and about 2:1.

In the context of the present invention, the crosslinking reaction is substantially instantaneous. In certain embodiments, the crosslinking reaction can occur within a timeframe of from about 1 second to about 5 minutes, for example from about 3 seconds to about 1 minute, for about 10 seconds to about 2 minutes, for example the gelation time may be less than about 30 seconds, or less than about 20 seconds, or yet less than about 10 seconds. For example, the crosslinking reaction can occur within a timeframe of about 10 seconds.

If desired, following preparation in vitro, a dynamic covalent hydrogel may be sterilized using any suitable method known in the art, such as gamma irradiation, autoclaving, ethylene oxide sterilization, infrared irradiation and electron-beam irradiation. A sterilization method is suitable to be used if it does not induce significant loss of useful physical and/or mechanical properties of the hydrogel. It is within the capabilities of one skilled in the art to select a suitable sterilization method.

A dynamic covalent hydrogel prepared in vitro may be stored under sterile conditions at low temperature (for example 4° C.) before being used.

3. Properties of Dynamic Covalent Hydrogels

A dynamic covalent hydrogel according to the present invention may be characterized by its viscoelasticity. The term "viscoelastic", as used herein to characterize a hydrogel, is meant to refer to a characteristic provided by a scaffold that can vary with a time and/or rate of loading. It is thus envisioned that appropriately viscoelastic hydrogels provide time and/or rate of loading characteristics that match or approximate that observed in a predetermined tissue or site (see below). This characteristic pertains to dissipation of energy, which can be provided by the scaffold itself and/or by the scaffold as a composite with cells growing therein. For example, it can be desirable to provide a scaffold that approximates the viscoelastic properties of the tissue which the hydrogel is intended to repair, restore or replace (see below).

A dynamic covalent hydrogel according to the present invention may have a shear storage modulus (G') comprised between about 10 Pa and about 10,000 Pa, preferably comprised between about 100 Pa and about 1000 kPa; and a shear loss modulus (G") comprised between about 0.01 Pa and about 1000 Pa, preferably comprised between about 0.1 kPa and about 500 Pa. Measurements of G' and G" values of a dynamic gel are typically performed on a range of frequencies comprised between 0.001 and 1000 Hz, and using a stress constraint comprised between 0.1 and 10 Pa.

A dynamic covalent hydrogel according to the present invention undergoes minimal swelling and exhibits high stability. As used herein, the term "swelling" is to be understood to be the property of a hydrogel to increase in weight and in volume when the hydrogel absorb fluid (here water). As used herein, the term "swelling ratio" refers to a ratio of the weight of a hydrogel when substantially completely hydrated to its weight when non-swollen (i.e., its weight before being immersed in the fluid). Swelling ratios are generally provided as percentages. Those skilled in the art know of suitable processes and measurement methods for determining swelling ratio. As used herein, the term "stability", when referred to a hydrogel, means absence of change in swelling ratio over time. A dynamic covalent hydrogel according to the present invention has a swelling ratio comprised between about 100% and about 300%, for example comprised between about 100% and about 200%. In the experiments presented in the Examples section below (see Example 1), stability of the prepared dynamic covalent hydrogels was observed for 35 days (for a 35 day-long experiment). It is highly probable a dynamic covalent hydrogel according to the present invention is stable for several weeks and up to several months.

4. Additional Components

Depending on the intended use of a dynamic covalent hydrogel according to the present invention, the hydrogel may comprise cells, a bioactive agent, a visualization agent, or any other additional ingredient, or a combination thereof. Examples of such cells and additional ingredients are provided below (see Pharmaceutical Compositions and Kits).

The bioactive agent, visualization agent or any other additional ingredient may be incorporated into a hydrogel before, during or after crosslinking of the first and second hydrogel precursor polymers. For example, before the crosslinking step, any additional ingredient may typically be added to at least one of the first and second hydrogel precursor solutions (as indicated above). During the crosslinking step, any additional ingredient may be added to the reaction mixture composed of the first and second hydrogel precursors. Alternatively, or additionally, a bioactive agent, visualization agent or any other active ingredient may be incorporated into a hydrogel after its formation. For example, a dynamic covalent hydrogel according to the present invention may be immersed in a solution containing any additional active ingredient to allow for diffusion of the ingredient into the hydrogel, or any additional active ingredient may be added to a solution containing a dynamic covalent hydrogel. Alternatively, a dynamic covalent hydrogel prepared from a crosslinking pair of hydrogel precursors wherein the first hydrogel precursor or the second hydrogel precursor is directly or indirectly covalently linked to a bioorthogonal functional moiety or to a clickable moiety (see above), may undergo a bioorthogonal or click conjugation to introduce a desired molecule or biomolecule (e.g., peptides, growth factors, drugs, fluorophores, and the like).

In embodiments where a dynamic covalent hydrogel according to the present invention comprises cells, the cells may be encapsulated within the hydrogel. As used herein, the term "encapsulated" has its art understood meaning, and refers to the containment, immobilization and/or entrapment of a cell or cells within a three-dimensional structure delineated by a physical barrier (i.e., a barrier that reduces or controls the permeability of said structure).

III—Uses of the Hydrogel Precursor Polymeric Compositions and Dynamic Covalent Hydrogels Soft materials such as injectable hydrogels have enabled diverse modern technologies including tissue engineering, cell therapy, drug delivery, biomedical devices, microfluidics, optics, stretchable and bio-integrated electronics, and soft robotics (see, for example, Yannas et al., Science, 1982, 215: 174-176; Lee and Mooney, Chem. Rev., 2001, 101: 1869-1880; Peppas et al., Adv. Mater., 2006, 18: 1345-1360; Jeong et al., Cell, 2015, 162: 662-674; Park et al., Nature Biotechnology, 2015, 33: 1280-1286; Whitesides, Nature, 2006, 442: 386-373; Casavant et al., PNAS USA, 2013, 110: 10111-10116; Dong et al., Nature, 2006, 42: 551-554; Choi et al., Nature Photonics, 2013, 7: 987-994; Choi et al., Advanced Materials, 2015, 27: 4081-4086; Kim et al., Science, 2008, 320: 507-511; Rogers et al., Science, 2010, 327: 1603-1607; Xu et al., Science, 2014, 344: 70-74; Tee et al., Science, 2015, 350: 313-316; Shepherd et al., PNAS USA, 201, 108: 20400-20403; and Morin et al., Science, 2012, 337: 828-832). Thus, the polymer compositions and dynamic covalent hydrogels according to the present invention can find application in a wide variety of fields, in particular in the treatment or prevention of a disease or medical condition in a subject.

As used herein, the term "subject" refers to a human or another mammal (e.g., primate, dog, cat, goat, horse, pig, mouse, rat, rabbit, and the like) that may or may not have a disease or disorder. Non-human subjects may be transgenic or otherwise modified animals. In many embodiments of the present invention, the subject is often referred to as an "individual" or a "patient". The terms "subject", "individual" and "patient" do not denote a particular age, and thus encompass newborns, children, teenagers, and adults. The term "patient" more specifically refers to an individual suffering from a disease or disorder.

The term "treatment" is used herein to characterize a method or process that is aimed at (1) delaying or preventing the onset of a disease, disorder or condition; (2) slowing down or stopping the progression, aggravation or deterioration of the disease, disorder or condition; (3) bringing about amelioration of the symptoms of the disease, disorder or condition; or (4) curing the disease, disorder or condition. A treatment may be administered after initiation of the disease, disorder or condition, for a therapeutic action. Alternatively, a treatment may be administered prior to the onset of the disease, disorder or condition, for a prophylactic or preventive action. In this case, the term "prevention" is used.

1. 3D Cell Culture and Cell Therapy

Dynamic covalent hydrogels of the present invention are attractive 3D cell culture alternatives to natural, animal-derived matrices such as MATRIGEL®. 3 D cell culture is an artificially created environment in which biological cells are permitted to grow or interact with their surroundings in all three dimensions, similar to how they would in vivo. In comparison to conventional cultures, cells in 3D cultures more closely resemble the in vivo situation with regards to cell shape and cellular environment. Architectural and material diversity is much greater on 3D matrices than on 2D substrates. Thus, in certain embodiments, dynamic covalent hydrogels of the present invention are used for 3D cell culture.

The expression "cell culture" refers to the process of keeping cells in conditions appropriate for maintenance and/or growth, where conditions refers, for example, to the temperature, nutrient availability, atmospheric $CO_2$ content and cell density in which the cells are kept. In hydrogels, cells can be cultured in vitro or in vivo. The appropriate culturing conditions for maintaining proliferating, expanding and differentiating different types of cells are well-known and documented. Cells that can be cultured using a dynamic covalent hydrogel according to a method of the present invention include any cell that can be grown in a 3D hydrogel matrix (see below).

Dynamic covalent hydrogels used for 3D cell culture may comprise any of a variety of biomolecules, the presence of which is desirable in a cell culture context. Examples of such biomolecules include, but are not limited to, proteoglycans or glycosaminoglycan chains, hormones, growth factors, chemoattractants, and the like (see Pharmaceutical Compositions and Kits below).

After being cultured in a dynamic covalent hydrogel according to the invention, cells may be harvested before being used. The term "harvesting", as used herein, refers to the action of detaching or dissociated the cells from the 3D hydrogel in which they have been cultured. Cells may be separated from hydrogel fragments resulting from enzymatic degradation of the hydrogel by filtration. Examples of enzymes that can be used to degrade the hydrogel scaffold include, but are not limited to, collagenase, elastase, trypsin, pullulanase, hyaluronidase, chondroitinase (ABC), cellulase, and the like. Alternatively, dynamic gels have the great advantage of breaking down in the presence of a large quantity of one of the two reactive groups in the form of small free molecules. Typically, adding glucamine or any other diol dissolves the gel and allows the cell to be retrieved by centrifugation without using an enzymatic reaction or trituration of the material.

After being harvested, cells cultured in a dynamic covalent hydrogel may find many applications. Thus, for instance, harvested cells may be used in cell therapy, wherein living cells are injected, grafted or implanted into a subject with the goal of treating or preventing a disease or medical condition in the subject. Thus, harvested cells may be used in the treatment of human clinical conditions (e.g., cancer, infectious diseases, autoimmune diseases) or in regenerative medicine (e.g., for the restoration and repair of damaged, injured or defective tissues such as cartilage in joint, spinal cord, and the like). The availability of large quantities of functioning stem cells, which have been proposed as promising candidates for therapies, could facilitate the development of autologous (from the patient) or allogeneic (from another donor) transplantations. Similarly, using dynamic covalent 3D hydrogel matrices of the present invention, large quantities of cells from genetically-customized stem cell lines could be produced for cell-based therapy. A dynamic covalent 3D hydrogel described herein can also be used for the proliferation of stem cells in therapeutic cloning (also called somatic cell nuclear transfer).

Alternatively, harvested cells may be used in tissue engineering applications. The availability of large quantities of functional cells is also an advantage in cell biology research. Other potential uses of a dynamic covalent hydrogel according to the present invention include, but are not limited to, production of lineage dependent viruses, e.g., for the production of viruses that require differentiated cells to yield sufficient particles for use as a vaccine; and protein manufacturing (where cells on the hydrogel produce a factor that can be isolated from the medium and/or from the cells and then purified). Examples of proteins that can be produced this way include, but are not limited to, growth factors, hormones, signal molecules, inhibitors of cell growth, and antibodies.

2. Tissue Engineering, Organoid Formation and Applications

Dynamic covalent hydrogels of the present invention may be used in tissue engineering. Tissue engineering is generally defined as the creation of tissue or organ equivalents by seeding of cells onto or into a scaffold suitable for implantation. Tissue engineering involves the use of a tissue scaffold for the formation of new viable tissue to repair or replace whole tissues or tissue portions (e.g., bone, cartilage, blood vessels, bladder, skin, muscle, etc.) damaged through diseases, trauma, genetic or chromosomal disorders, or aging. Thus, in certain embodiments, dynamic covalent hydrogels described herein are used in tissue engineering.

As known in the art, it is necessary to perform tissue culture in a suitable culture medium with or without stimulus such as stress or orientation. In addition, a tissue culture medium or the dynamic covalent hydrogel may comprise any of a variety of biomolecules, the presence of which is desirable in such a context. Examples of such biomolecules include growth factors, nutrients and/or cell binding domains, saccharides, tissue adhesives and the like.

Examples of tissue equivalents include organoids. As used herein, the term "organoids" refers to three-dimensional culture systems of organ-specific cell types that develop from stem cells and self-organize (or self-pattern) through cell sorting and spatially restricted lineage commitment in a manner similar to the situation in vivo. An organoid therefore represents the native physiology of the cells and has a cellular composition (including remaining stem cells and specialized cell types) and anatomy that emulate the native situation. The cells from which an organoid is generated differentiate to form an organ-like tissue exhibiting multiple cell types that self-organize to form a structure very similar to the organ in vivo. Organoids are therefore excellent models for studying human organs and human organ development in a system very similar to development in vivo. Organoids may be used for drug response screening, toxicity assays, or regenerative medicine. Organoids can also be used to culture pathogens such as noroviruses for which there are currently no suitable tissue cultures or animal models.

3. In Vivo Delivery of Cells and/or Bioactive Agents

In certain embodiments, dynamic covalent hydrogels according to the present invention may be used as systems for the delivery of cells and/or bioactive agents in vivo (i.e., in the body of a subject in need thereof).

In certain embodiments, a hydrogel according to the present invention may be used for cell delivery. Hydrogels of the invention may be used as a raw material for preparing cell delivery systems that can be administered to a subject for therapeutic or diagnostic purposes. In certain embodiments, hydrogels of the invention may be used to prepare a patch, a biofilm or a dressing that can be loaded with cells. For example, hydrogels according to the present invention may be used to prepare a dressing that can be applied on the skin, for reconstructing or healing the skin (for example at a site of damaged or wounded skin). Alternatively, said dressing may be applied on the heart of a subject for treating ischemia (myocardial infarction). In such embodiments, the cells that are entrapped in the hydrogel can migrate into the targeted tissue or organ.

In other embodiments, a crosslinking pair of hydrogel precursor polymers may be used for cell delivery. Indeed, in situ gelling polymeric matrices are of great interest in tissue regeneration since these materials can be used as injectable hydrogels. They can act as cell vehicles that have the ability to take the shape of the corresponding tissue cavity. Furthermore, problems related to cell adhesion can be minimized since cells can directly be incorporated into the injectable solution.

Dynamic covalent hydrogels and pairs of hydrogel precursor polymers according to the present invention can be used as vehicles for the delivery and/or the controlled release of at least one bioactive agent. The terms "bioactive agent" and "biologically active agent" are used herein interchangeably; and include, without limitation, physiologically or pharmacologically active substances that act locally or systemically in the body, such as therapeutic, prophylactic, and/or diagnostic agents, substances that affect the structure or function of the body (for example that affect or participate in tissue growth or cell differentiation), compounds that are able to invoke a biological action such as an immune response or that may play any other role in one or more biological processes, prodrugs that become biologically active or more active after they have been placed in a predetermined physiological environment, as well as compounds or agents that support or favor cell growth, cell differentiation and/or cell implantation. Examples of bioactive agents are given below (see Pharmaceutical Compositions and Kits).

A bioactive agent may be admixed with, covalently bonded to and/or adsorbed in or on the hydrogel. Alternatively, or additionally, a bioactive agent is comprised in a solution of the first hydrogel precursor polymer or of the second hydrogel precursor polymer of a crosslinking couple used to form a dynamic covalent hydrogel, such that after crosslinking of the first and second polymers, the dynamic covalent hydrogel thus formed comprises the bioactive agent.

4. Viscosupplementation/Artificial Joint Lubricant

In certain embodiments, a crosslinking pair of hydrogel precursor polymers or a dynamic covalent hydrogel according to the present invention may be used in viscosupplementation. Viscosupplementation is a procedure that involves the injection of gel-like substances (e.g., hyaluronates) into a joint to supplement the viscous properties of synovial fluid. Injection of viscoelastic fluids, most commonly crosslinked hyaluronic acid, into joints has been performed for over 20 years in the treatment of osteoarthritis. These viscosupplementation treatments are said to derive their effectiveness in part from the high viscosity of the injected polymer solution.

Polymeric hydrogels which undergo crosslinking during or after administration to a joint space may represent an improvement because such hydrogels undergo an increase in viscosity within the joint space following administration. Thus, crosslinking pairs of hydrogel precursor polymers according to the present invention may be administered as a relatively less viscous liquid, then forming a much more viscous or viscoelastic gel in the intra-articular space of a joint within a short timeframe. Additionally, the higher viscosity imparted by crosslinking in situ can lead to prolonged residence time in the joint and therefore longer treatment duration achieved with a single administration.

Thus, a crosslinking pair of hydrogel precursor polymers or a dynamic covalent hydrogel according to the present invention may be used in viscosupplementation for the treatment of osteoarthritis or rheumatoid arthritis, or of other inflammatory arthritides such as gout or calcium pyrophosphate deposition disease (e.g., by injection into the intra-articular space of a joint). Joints include knee, shoulder, temporomandibular and carpometacarpal joints, elbow, hip, wrist, ankle, and lumbar zygapophysial (facet) joints in the spine.

In certain embodiments, at least one of the hydrogel precursor polymer solutions comprises a corticosteroid (such as triamcinolone acetonide, cortisone acetate) which is useful for providing relief of pain and of swelling due to inflammation experienced by a subject suffering from osteoarthritis. Several advantages are associated with the entrapment/incorporation of a corticosteroid within a hydrogel in situ: the trapping (1) is effective to prevent direct contact of the majority of the steroid with the joint tissues; (2) is effective to maximize the localized concentration of the steroid in the joint, while minimizing its systemic concentration, (3) is effective to protect the steroid from premature clearance from the joint, and (4) allows to attain therapeutic efficacy at a lower total dose than would be attained in the absence of hydrogel entrapment, while minimizing unwanted local and systemic side effects.

In certain embodiments, at least one of the hydrogel precursor polymer solutions comprises a fibroblast growth medium to revitalize the cellular components of the articular connective tissues, particularly synoviocytes and chondrocytes, and consequently ensure their cellular regeneration and stimulate their endogenous synthesis The viscosupplementation may be accomplished via a single injection or multiple intra-articular injections administered over a period of weeks into the afflicted joint(s). The goal is to provide a joint with a capability of absorbing shocks during a movement and of being lubricated at least at rest. In certain embodiments, viscosupplementation is administered with the goal of delaying total hip arthroplasty or total knee arthroplasty.

5. 3D-Printing and 3D-Bioprinting

In certain embodiments, crosslinking pairs of hydrogel precursor polymers and dynamic covalent hydrogels described herein find application in 3D-printing or 3D-bioprinting. 3D printing builds a three-dimensional object from a computer-aided design model, usually by successively adding material layer by layer. 3D-Bioprinting utilizes 3D printing technology to produce functional miniaturized tissue constructs from biocompatible materials, cells and supporting components such as cell media. Major applications include use in high-throughput in vitro tissue models, drug discovery and toxicology, regenerative medicine/tissue engineering applications. It involves layer-by-layer, precise positioning of the biomaterials and living cells, with spatial control of the placement of functional components. The technology has made significant progress towards the clinical restoration of tissues and organs such as ear, nose, bone, heart, liver and skin.

6. Soft Robotics

Crosslinking pairs of hydrogel precursor polymers and dynamic covalent hydrogels described herein may be applied in soft robotics. Soft robotics is a specific subfield of robotics dealing with constructing robots from highly compliant materials, similar to those found in living organisms (Robosoft, first IEEE International Conference on Soft Robotics, Apr. 24-28, 2018, Livorno, Italy). In contrast to robots built from rigid materials, soft robots allow for increased flexibility and adaptability for accomplishing tasks, as well as improve safety when working around humans. These characteristics allow for its potential use in the fields of medicine and manufacturing. Thus, for example, soft robots can be implemented in the medical profession, specifically for invasive surgery. Soft robots can be made to assist surgeries due to their shape changing properties. Shape change is important as a soft robot could navigate around different structures in the human body by adjusting form.

IV—Pharmaceutical Compositions and Kits

In order to use crosslinking pairs of hydrogel precursor polymers and dynamic covalent hydrogels as described herein for therapeutic treatment of mammals, including humans, in some embodiments, the hydrogel precursor polymers and dynamic covalent hydrogels are formulated in accordance with standard pharmaceutical practice as a pharmaceutical composition. Thus, the present invention provides a pharmaceutical composition comprising a dynamic covalent hydrogel described herein and at least one pharmaceutically acceptable diluent or carrier. The present invention also provides a pharmaceutical composition, wherein the first hydrogel precursor polymer of a crosslinking pair described herein is formulated with at least one pharmaceutically acceptable diluent or carrier and the second hydrogel precursor polymer of the crosslinking pair described herein is formulated with at least one pharmaceutically acceptable diluent or carrier.

Pharmaceutical compositions according to the present invention can be prepared, packaged, and/or sold in bulk, as a single unit dose, and/or as a plurality of single unit doses. As used herein, the term "unit dose" refers to a discrete amount of the pharmaceutical composition comprising a predetermined amount of each of the hydrogel precursor polymers or a predetermined number of a dynamic covalent hydrogel of given shape and dimensions.

A pharmaceutical composition according to the present invention is formulated, dosed and administered in a fashion, i.e., amounts, concentrations, schedules, course, vehicles and route of administration, that is consistent with good medical practice. Factors to be taken into consideration in this context include, the particular disease or clinical condition to be treated, the particular subject being treated (age, weight, etc), the clinical condition (health status) of the individual patient, the cause of the disorder, the site of delivery of the composition, the method of administration, the scheduling of administration, and other factors known to medical practitioners.

1. Formulations

As used herein, the term "pharmaceutically acceptable carrier or excipient" refers to a carrier medium which does not interfere with the effectiveness of the biological activity of the active ingredient(s) and which is not excessively toxic to the host at the concentration at which it is administered. The term includes solvents, dispersion media, antibacterial and antifungal agents, isotonic agents, and the like. The use of such media and agents for pharmaceutically active substances is well known in the art (see for example "*Remington's Pharmaceutical Sciences*", E. W. Martin, $18^{th}$ Ed., 1990, Mack Publishing Co.: Easton, PA, which is incorporated herein by reference in its entirety).

Examples of suitable pharmaceutically acceptable carrier or excipient include, but are not limited to, saline and/or buffers (e.g., citrate buffer solutions, acetate buffer solutions, phosphate buffer solutions, and the like), antioxidants (e.g., ascorbic acid, alpha tocopherol, ascorbyl palmitate, methionine, and the like), preservatives, low molecular weight (less than 10 residues) peptides, proteins (e.g., serum albumin, gelatin or immunoglobulins), hydrophilic polymers (e.g., polyvinylpyrrolidone), amino acids (e.g., glycine, glutamine, asparagine, histidine, arginine, or lysine), monosaccharides, disaccharides and other carbohydrates (e.g., glucose, mannose or dextrins), chelating agents (e.g., EDTA, citric acid and salts and hydrates thereof, fumaric acid and salts and hydrates thereof, malic acid and salts and hydrates thereof, and the like), sugars (e.g., sucrose, mannitol, trehalose, sorbitol), salt-forming counterions (e.g., sodium), non-ionic surfactants (e.g., TWEEN™, PLURONICS™, polyethylene glycol), lubricating agents (e.g., magnesium stearate, calcium stearate, stearic acid, silica, talc, malt, glyceryl behanate, natural oils, polyethylene glycol, sodium benzoate, sodium acetate, sodium chloride, leucine, magnesium lauryl sulfate, sodium lauryl sulfate, and the like), and any combination thereof.

Suitable preservatives may be antimicrobial preservatives (e.g., benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal), antifungal preservatives (e.g., butyl paraben, methyl paraben, ethyl paraben, propyl paraben, benzoic acid, hydroxybenzoic acid, potassium benzoate, potassium sorbate, sodium benzoate, sodium propionate, and sorbic acid), antiprotozoan preservatives, alcohol preservatives (e.g., ethanol, polyethylene glycol, phenol, phenolic compounds, bisphenol, chlorobutanol, hydroxybenzoate, and phenylethyl alcohol), acidic preservatives (e.g., vitamin A, vitamin C, vitamin E, beta-carotene, citric acid, acetic acid, dehydroacetic acid, ascorbic acid, sorbic acid, and phytic acid), any other preservatives known to be useful in pharmaceutical compositions (e.g., tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, and the like), and any combination thereof.

For example, injectable preparations can be formulated according to the known art using suitable vehicles and solvents such as water, Ringer's solution, U.S.P. and isotonic sodium chloride solution. In addition, sterile, fixed oils are conventionally employed as a solution or suspending medium. For this purpose, any bland fixed oil can be employed including synthetic mono- or di-glycerides. Fatty acids such as oleic acid may also be used in the preparation of injectable formulations. Sterile liquid carriers are useful in sterile liquid form compositions for administration by injection. Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. Where necessary or desired, an injectable formulation may include a local anesthetic to ease pain at the site of injection.

When applied topically, the crosslinking pairs of hydrogel precursor polymers and the dynamic covalent hydrogels according to the invention, for example comprising cells and/or bioactive agents, are suitably combined with other ingredients, such as carriers and/or adjuvants. There are no limitations on the nature of such other ingredients, except that they must be physiologically acceptable and efficacious for their intended administration and cannot degrade the activity of the active ingredients of the composition. In certain embodiments, a pharmaceutical composition according to the present invention may be impregnated into, or deposited onto, articles which can include, for example, transdermal patches, plasters and bandages. In other embodiments, crosslinking pairs of hydrogel precursor polymers and dynamic covalent hydrogels according to the invention may be used to prepare a patch, a biofilm or a dressing that can be loaded with cells and/or bioactive agents.

Although the description of compositions provided herein are principally directed to compositions which are suitable for administration to humans, it will be understood by those skilled in the art that such compositions are generally suitable for administration of animals of all sorts. Modification of compositions suitable for administration to humans in order to render the compositions suitable for administration to various animals is well understood.

2. Additional Components

A pharmaceutical composition according to the present invention may further comprise at least one additional component selected from cells, biologically active agents, visualization agents, or any combination thereof. As already mentioned above, biologically active agents and visualization agents may be associated, either covalently or ionically, with at least one of the hydrogel precursor polymers or with the dynamic covalent hydrogel present in the pharmaceutical composition. Alternatively, or additionally, biologically active agents and visualization agents may be mixed with a hydrogel precursor solution or a pharmaceutical composition according to the present invention and do not form any association with a hydrogel precursor polymer or with the hydrogel.

A. Cells

In certain embodiments, a hydrogel precursor polymer solution or a dynamic covalent hydrogel contains cells. As used in the context of the present invention, the term "cells" refers to cells in various forms, including but not limited to cell clusters (such as pancreatic islets or portions thereof) and individually isolated cells. In certain preferred embodiments, cells to be used in association with a hydrogel precursor polymer solution or a dynamic covalent hydrogel according to the present invention are of mammalian (animal or human) origin. Mammalian cells may be of any organ, fluid or tissue origin (e.g., brain, liver, skin, lung, kidney, heart, muscle, bone, bone marrow, blood, amniotic fluid, umbilical cord blood, etc) and of any cell type (see below). Cells may be primary cells, secondary cells or immortalized cells (i.e., established cell lines). They may be isolated or derived from ex vivo biological samples or obtained from volunteers or patients by techniques well known in the art. Cells used in regenerative medicine and tissue engineering can come from the patient to which cells are to be administered (autologous administration) or from other individual(s) (allogeneic administration). In addition, xenogeneic cells such as those from animals can also be adopted in regenerative medicine strategies. Alternatively, cells may be purchased from commercial sources (for example, from the American Type Culture Collection, Manassas, VA). Alternatively, or additionally, cells may be genetically engineered to contain a gene of interest such as a gene expressing a growth factor or a receptor, or to contain a defective gene, or yet to contain Oct3/4, Sox2, Klf4, and c-Myc genes in order to prepare human induced stem cells from adult somatic cells.

Cells that may be used in combination with a hydrogel precursor polymer solution or a dynamic covalent hydrogel described herein include differentiated cells, stems cells (including induced pluripotent stem cells), and progenitor cells.

As used herein, the term "differentiated cells" refers to cells that are specialized for a particular function and that do not have the ability to generate other kinds of cells. Examples of differentiated cells include, but are not limited to, basal cells, epithelial cells, platelets, lymphocytes, T-cells, B-cells, natural killer cells, reticulocytes, granulocytes, monocytes, mast cells, neurocytes, neuroblasts, glioblastom, cytomegalic cells, dendritic cells, macrophages, blastomeres, endothelial cells, interstitial cells, Kupffer cells, Langerhans cells, littoral cells, and tissue cells. Specific examples of differentiated cells include, but are not limited to, fibroblasts, chondrocytes, osteoblasts, osteoclasts, osteocytes, synovial cells, bone marrow stromal cells, stem cells, fibrocartilage cells, endothelial cells, smooth muscle cells, adipocytes, cardiomyocytes, myocytes, keratinocytes, hepatocytes, leukocytes, macrophages, endocrine cells, genitourinary cells, lymphatic vessel cells, pancreatic islet cells, muscle cells, intestinal cells, kidney cells, blood vessel cells, thyroid cells, parathyroid cells, cells of the adrenal-hypthalamic pituitary axis, bile duct cells, ovarian or testicular cells, salivary secretory cells, renal cells, epithelial cells, and nerve cells.

As used herein, the term "stem cells" refers to relatively undifferentiated cells that have the capacity for sustained self-renewal as well as the potential to give rise to differentiated progeny (i.e., to different types of specialized cells). Examples of stems cells include, but are not limited to, embryonic stem cells, adult stem cells and induced pluripotent stem cells. The terms "embryonic stem cells" and "ES cells" are used herein interchangeably. They refer to stem cells derived from a group of cells called the inner cell mass, which is part of the early (4 to 5 days old) embryo called the blastocyst. "Human embryonic stem cells" or "hES cells" are embryonic stem cells of human origin that are generally derived from fertilized embryos that are less than one week old. In vitro, embryonic stem cells can proliferate indefinitely, a property that is not shared by adult stem cells. The term "adult stem cells" refers to stem cells that are not embryonic in origin nor derived from embryos or fetal tissue. The term "adult stem cells" also encompasses stem cells isolated from subjects of all ages (e.g., human infants and children). As used herein, the term "induced pluripotent stem cells" (or "iPS cells") refers to a type of pluripotent stem cells artificially derived from non-pluripotent cells (e.g., adult somatic cells). Induced pluripotent stem cells are identical to embryonic stem cells in their ability to form any differentiated cell but are not derived from an embryo. The induced pluripotent stem cells may be human induced pluripotent stem cells. The terms "human induced pluripotent stem cells" and "human iPS cells" are used herein interchangeably. They refer to induced pluripotent stem cells of human origin. Typically, a human induced stem cell may be obtained through the induced expression of Oct3/4, Sox2, Klf4, and c-Myc genes in any adult somatic cell (e.g., fibroblast). Basically, somatic cells are transfected with viral vectors, such as retroviruses, which comprise Oct3/4, Sox2, Klf4, and c-Myc genes.

The terms "progenitor cells" and "precursor cells" are used herein interchangeably. They refer to cells that occur in fetal or adult tissue and are partially specialized. These cells divide and give rise to differentiated cells. Progenitor or precursor cells belong to a transitory amplifying population of cells derived from stem cells. Compared to stem cells, they have a limited capacity for self-renewal and differentiation. Such capacity for self-renewal (or proliferation) is demonstrated by the expression of proliferation markers such as, for example, Ki-67 nuclear antigen. Moreover, since progenitor cells are committed to a particular differentiation process, progenitor cells also express specific markers. Examples of progenitor cells include, but are not limited to, hematopoietic progenitor cells, endothelial progenitor cells, neural progenitor cells, mesenchymal progenitor cells, osteogenic progenitor cells, stromal progenitor cells, and the like.

Cells present in a hydrogel precursor polymer solution or a dynamic covalent hydrogel may form a substantially homogenous population or a heterogeneous cell population. The term "substantially homogeneous cell population", as used herein, refers to a population of cells wherein the majority (e.g., at least about 90%, preferably at least about 95%, more preferably at least about 99%) of the total number of cells belong to a single cell type. The term "heterogeneous cell population", as used herein, refers to a population of cells comprising at least two cell types.

Cells may be present in a hydrogel precursor polymer solution or a dynamic covalent hydrogel at any suitable amount. For example, cells may be added to a hydrogel precursor polymer solution or a dynamic covalent hydrogel at a cell density of about 500 to about 1000 cells/μL.

B. Bioactive Agents

In certain embodiments, a pharmaceutical composition according to the present invention comprises at least one bioactive agent. As will be appreciated by one skilled in the art, selection of one or more bioactive agents will be based on the intended purpose of the pharmaceutical composition (e.g., use in viscosupplementation, in the treatment of joints, in cell therapy, in 3D cell culture, in tissue engineering, etc). In general, the amount of bioactive agent present in an inventive pharmaceutical composition will be the ordinary dosage required to obtain the desired result through a given route of administration. Such dosages are either known or readily determined by a skilled practitioner in the pharmaceutical and/or medical arts.

Suitable bioactive agents may belong to a wide variety of classes of molecules including, but not limited to, small-molecule drugs, peptides, polypeptides, proteins, antibodies, genes and gene products, carbohydrates, monosaccharides, oligosaccharides, polysaccharides, nucleoproteins, mucoproteins, lipoproteins, glycoproteins, oligonucleotides, steroids, nucleic acids, DNAs, RNAs, aptamers, nucleodides, nucleosides, oligonucleotides, antisense oligonucleotides, polynucleotides, siRNA, lipids, hormones, vitamins, and combinations thereof. A bioactive agent may be a single compound or a plurality of compounds including, for example, combinations of two or more bioactive agents.

Examples of suitable therapeutic agents include, but are not limited to, analgesics, anesthetics, pain-relieving agents, anticancer agents, antimicrobial agents, antibacterial agents, antiviral agents, antifungal agents, antibiotics, anti-inflammatory agents, antioxidants, antiseptic agents, antipruritic agents, immunostimulating agents, antiangiogenesis agents, antineoplastic agents, antiproliferative agents, antidiabetic agents, decongestants, antihypertensive agents, dermatological agents, anticholinergics, immunosuppressants, antidepressant, antipsychotics, β-adrenergic blocking agents, cardiovascular active agents, vasoactive agents, non-steroidals, sex hormones, steroid agents, osteogenic agents, osteoconductive agents, osteoinductive agents, anti-rejection agents, antiarthritic agents, thrombolytic agents, antifibrinolytic agents, hemorheologic agents, antiplatelet agents, and the like.

Other examples of suitable bioactive agents include cytokines, growth factors, proteoglycans or portions thereof, adhesion molecules, and any combination thereof.

Cytokines and growth factors are polypeptide molecules that regulate migration, proliferation, differentiation and metabolism of mammalian cells. A diverse range of these biomolecules have been identified as potentially playing an important role in regulating healing. Cytokines may be lymphokines, monokines or chemokines. Examples of cytokines include, but are not limited to, interleukins (ILs) (e.g., IL-1, IL-2, IL-4 and IL-8), interferons (IFNs) (e.g., IFN-α, IFN-β, and IFN-γ), and tumor necrosis factors (e.g., TNF-α), or any variants, synthetic analogs, active portions or combinations thereof. Examples of growth factors include, but are not limited to, epidermal growth factors (EGFs), platelet-derived growth factors (PDGFs), heparin binding growth factor (HBGFs), fibroblast growth factors (FGFs), vascular endothelial growth factors (VEGFs), insulin-like growth factors (IGFs), connective tissue activating peptides (CTAPs), transforming growth factors alpha (TGF-α) and beta (TGF-β), nerve growth factor (NGFs), colony stimulating factors (G-CSF and GM-CSF), and the like, or any variants, synthetic analogs, active portions or combinations thereof.

Proteoglycans are protein-carbohydrate complexes characterized by their glycosaminoglycan (GAG) component. GAGs are highly charged sulfated and carboxylated polyanionic polysaccharides. Examples of GAGs suitable for use in pharmaceutical compositions of the present invention include, but are not limited to, hyaluronan, chondroitin sulfate, dermatan sulfate, heparan sulfate, and keratan sulfate.

Adhesion molecules constitute a diverse family of extracellular and cell surface glycoproteins involved in cell-cell and cell-extracellular matrix adhesion, recognition, activation, and migration. Adhesion molecules are essential to the structural integrity and homeostatic functioning of most tissues and are involved in a wide range of biological processes, including embryogenesis, inflammation, thrombogenesis, and tissue repair. Adhesion molecules include matricellular proteins (e.g., thrombospondins, and tenascins), and cell surface adhesion molecules (e.g., integrins, selectins, cadherins, and immunoglobulins).

Other examples of bioactive agents include, but are not limited to, hormones and hormone analogs (e.g., growth hormone), morphogens (e.g., retinoic acid, arachidonic acid, and the like), extracellular matrix molecules (e.g., fibronectin, vitronectin, laminin, collagen, elastin, and the like), blood clotting/coagulation factors (e.g., fibrinogen, prothrombin, hemophilia A, and the like); and the like.

Biologically active agents may be bioactive peptide sequences that can be attached to the surface of a hydrogel to facilitate protein adsorption and subsequent cell tissue attachment. Examples include adhesive peptides derived from fibronectin, vitronectin, laminin, and collagen. The term "RGD" or "RGD sequence" refers to a minimum bioactive RGD sequence, which is Arginine-Glycine-Aspartic Acid (RGD) sequence, and which is the smallest (minimal) fibronectin-derived amino acid sequence that is sufficient to mimic cell binding to fibronectin and/or to promote adhesion of the anchorage-dependent cells. Such short-chain RGD bioactive peptides are known in the art.

Exemplary diagnostic agents include paramagnetic molecules, fluorescent compounds, magnetic molecules, and radionuclides, x-ray imaging agents, and contrast agents.

In certain embodiments, bioactive agents are particles such as bioactive glass, soluble glass, resorbable calcium phosphate, hydroxyapatite, calcium carbonate, calcium sulphate, glass-ceramics, and the like.

In certain embodiments, the pharmaceutical compositions described herein contain less than about 80%, less than about 75%, less than about 70%, less than about 60%, less than about 50%, less than about 40%, less than about 30%, less than about 20%, less than about 15%, less than about 10%, less than about 5%, less than about 1%, less than about 0.5%, or less than about 0.1% by weight of bioactive agent(s).

C. Visualization Agents

In certain embodiments, a hydrogel precursor polymer solution or a dynamic covalent hydrogel may contain a visualization agent to improve visibility, for example to enable a surgeon to accurately and conveniently place an in situ forming hydrogel during a surgical procedure. Visualization agents may be selected from a variety of non-toxic colored substances, such as dyes suitable for use in implantable medical devices. Suitable dyes may include, for example, a dye for visualizing thickness of the hydrogel as it is formed in situ, such as for example FD&C Blue #1, FD&C Blue #2, FD&C Blue #3, D&C Green #6, methylene blue, indocyanine green, other colored dyes, and combinations thereof. Other visualization agents may be used such as fluorescent compounds (e.g., fluorescein or eosin), x-ray contrast agents (e.g., iodinated compounds), ultrasonic contrast agents, MRI contrast agents (e.g., Gadolinium containing compounds), PET agents (e.g., fluorodeoxyglucose or FDG). PS or SPECT agents (e.g., radioligands such as $^{11}$C-DASB, $^{11}$C-flumazenil, $^{11}$C-raclopride, and the like).

The visualization agent may be covalently linked to at least one of the hydrogel precursor polymers. However, in preferred embodiments, the visualization agent is not covalently linked to the hydrogel precursor polymer. For example, the visualization agent may be present in a precursor hydrogel solution. The visualization agent may be used in small quantities, for example in a concentration of less than 1% weight/volume, or of less than 0.01% weight/volume, or even of less than 0.001% weight/volume.

3. Administration

A pharmaceutical composition according to the present invention may be administered using any suitable administration route. Administration routes include, enteral (e.g., oral), parenteral, intravenous, intramuscular, intraarterial, intramedullary, intrathecal, subcutaneous, intraventricular, transdermal, interdermal, rectal, intravaginal, intraperitoneal, topical, mucosal, nasal, bucal, sublingual, and the like. Specifically, the preferred route in the context of the present invention is direct administration to an affected site (e.g., by transcutaneous injection, for example in the intra-articular space of a joint, by topical placement on a damaged or wounded skin site, by placement in combination with surgical procedure and the like).

Dynamic covalent hydrogels, that exhibit viscous flow under shear stress (shear thinning) and rapid recovery when the applied stress is relaxed (self-healing), allow for minimally invasive implantation in vivo through direct injection or catheter-based delivery. Thus, in certain embodiments, a dynamic covalent hydrogel according to the present invention may be compressed and loaded in to a delivery-device, such as a catheter, endoscope, syringe, or the like. The delivery-device is snaked through the vasculature or other vessel system of the intended patient host and the hydrogel is released from the delivery-device and optionally anchored (e.g., sutured onto the target repair or regeneration site). Once released at the site, the hydrogel expands resiliently to about its original, relaxed size and shape.

In other embodiments, the implantable hydrogel is inserted by an open surgical procedure.

As mentioned above, a dynamic covalent hydrogel according to the present invention may be formed in situ (e.g., directly at or in the vicinity of a given site in a living animal or human body). In this case, hydrogel formation is initiated by mixing the two hydrogel precursor polymers at the site of injection. Thus, in certain embodiments, the two hydrogel precursors of a crosslinking pair according to the present invention may be applied (e.g., injected) via a sprayer to the tissue to form a coating or space filling hydrogel in situ. Preferably, the two hydrogel precursors are placed in separate chambers of the sprayer. When the sprayer is activated, the emergent spray contacts tissue, resulting in mixing and crosslinking of the two hydrogel precursor polymers, gelation takes place and the hydrogel is formed at the intended site of the body. The sprayer may be a multi-barrel system, preferably a double-barrel syringe system.

As used herein, the term "multi-barrel system" refers to any system or device, usually a syringe, which comprises at least two separate barrels and may have two or more plungers. The term "double-barrel syringe system", as used herein, refers to any system or device, usually a syringe, which comprises two separate barrels and may have one or two plungers. In addition, the multi-barrel (e.g., double-barrel) syringe system generally comprises a tip cap, or a needle or cannula with or without a needle shield, in order to seal the end(s) of the syringe system. The barrels generally have the storage capacity for containing enough of the first and second hydrogel precursor solutions. The barrels may be made of glass, plastic, or any other suitable material and may have different geometries, inner diameters, material compositions, clearness, etc. Further, the multi-barrel syringe system may be a double-barrel syringe system in the form of a syringe having two integrally connected syringes, i.e., two integrally connected barrels, and a mono or double plunger assembly for dispensing the contents from the barrels. Also, the syringe system may include two detachably connected barrels and two or one detachably connected plungers. Furthermore, the syringe system may also include means (e.g., an applicator tip) configured for thoroughly mixing the components contained in the barrels before being dispensed through the applicator tip. Thus, the barrels are generally connected, and the plunger assembly is generally configured to dispense the contents from the barrels simultaneously, such that the appropriate mixing ratios of the hydrogel precursor solutions will be preserved.

A treatment according to the present invention may be administered in a single dose or in multiple doses (e.g., every day, every week, every month, every two months, every three months, every semester, every year, every two years, and the like). Doses and dose regimen will be decided by the medical practitioner.

A dose may be any amount of a pharmaceutical composition that is sufficient to achieve the desired biological or medical response. For example, a dose may correspond to between about 0.1 μg and about 1 μg of a crosslinking pair of hydrogel precursors or of a hydrogel, or between about 0.001 mg and about 0.01 mg, or between about 0.01 mg and about 0.1 mg, or between about 0.1 mg and about 1 mg, or between about 1 mg and about 3 mg, or between about 3 mg and about 10 mg, or between about 10 mg and about 30 mg, or between about 30 mg and about 100 mg, or between about 100 mg and about 300 g, or between about 300 mg and about 1,000 mg, or between about 1 g and about 10 g of a crosslinking pair of hydrogel precursors or of a hydrogel.

4. Kits

In another aspect, the present invention provides a pharmaceutical pack or kit comprising one or more containers (e.g., vials, ampoules, test tubes, flasks or bottles) containing one or more ingredients of an inventive pharmaceutical composition described herein.

Different ingredients of a pharmaceutical pack or kit may be supplied in a solid (e.g., lyophilized) or in liquid or semi-liquid form. Each ingredient will generally be suitable as aliquoted in its respective container or provided in a concentrated form. Packs or kits according to the present invention may include media for the reconstitution of lyophilized ingredients. Individual containers of the kits will preferably be maintained in close confinement for commercial sale.

In certain embodiments, a kit according to the present invention comprises a first hydrogel precursor polymer and a second hydrogel precursor polymer of a crosslinking pair as described herein, wherein the first and second hydrogel precursor polymers (as such or individually formulated in solution) are contained in different containers. In other embodiments, the first and second hydrogel precursor polymers are contained in a multi-barrel syringe system, preferably in a double-barrel system.

In certain embodiments, a kit according to the present invention comprises at least one dynamic covalent hydrogel contained in a first container and at least one medium and/or reagent to use the hydrogel. Examples of such media and/or reagents include, but are not limited to, rehydrating medium and/or reagents; antibiotics; biomolecules, biologically active agents as described herein, cell culture medium and/or reagents, cells, seeding means, harvesting medium and/or reagents, filters, washing medium and/or reagents, and the like.

In certain embodiments, a pack or kit includes one or more additional bioactive agent(s). Optionally associated with the container(s) can be a notice or package insert in the form prescribed by a governmental agency regulating the manufacture, use or sale of pharmaceutical or biological products, which notice reflects approval by the agency of manufacture, use or sale for human administration. The notice of package insert may contain instructions for use of the pair of hydrogel precursor polymers or of the dynamic covalent hydrogel according to methods of treatment disclosed herein.

An identifier, e.g., a bar code, radio frequency, ID tags, etc., may be present in or on the kit. The identifier can be used, for example, to uniquely identify the kit for purposes of quality control, inventory control, tracking movement between workstations, etc.

EXAMPLES

The following examples describe some of the preferred modes of making and practicing the present invention. However, it should be understood that the examples are for illustrative purposes only and are not meant to limit the scope of the invention. Furthermore, unless the description in an Example is presented in the past tense, the text, like the rest of the specification, is not intended to suggest that experiments were actually performed, or data were actually obtained.

Example 1

I. Synthesis and Polymer Modification—Synthesis of Aminated Wulff-Type B

Synthesis of (2-(((4-((tert-butoxycarbonyl)amino)butyl) amino)methyl)phenyl) boronic acid. To a solution of BOC-protected diaminobutane (BOC-DAB; 2.66 mmol; 500 mg) in 3 mL of methanol was added under argon 2-formylphenylboronic acid (1 eq; 2.66 mmol; 398 mg). After stirring at room temperature over 16 hours, sodium borohydride (4.26 mmol; 161 mg) was slowly added at 0° C. to the yellowish solution. The reaction mixture was then stirred at room temperature and monitored by TLC (dichloromethane/methanol (7/3, vol/vol)) until completion. After solvent removal under vacuum, the crude product was dissolved in a mixture of water (12 mL) and dichloromethane (25 mL). The aqueous phase was extracted 5 times with dichloromethane (5×12 mL). The resulting combined organic phases were dried over $MgSO_4$ and concentrated in vacuo, yielding the expected compound as a white solid (0.76 g; yield: 93%).

Synthesis of (2-(((4-aminobutyl)amino)methyl)phenyl) boronic acid. The above product was dissolved in 3 mL of methanol, and slow HCl gas bubbling was performed. The monitoring of the reaction was performed by $^1H$ NMR. After 30 minutes, the reaction mixture was concentrated in vacuo, yielding the corresponding ammonium salt. The obtained solid was dissolved in pure water (10 mL), and pH was adjusted to 11 by dropwise addition of NaOH (1 M). The reaction mixture was concentrated by co-solvent evaporation using toluene. The solid residue was partitioned by addition of dichloromethane. After drying over $Na_2SO_4$ and filtration, the organic phase was concentrated in vacuo, yielding the expected aminated Wulff-type phenylboronic acid derivative as a yellowish powder (427 mg; 72%).

Synthesis of boronic acid-modified polysaccharide. A typical synthesis was as follows: 500 kDa hyaluronic acid (HA) (100 mg) was dissolved in MES buffer pH 5.5 (10 mL). DMT-MM (4-(4,6-dimethoxy-1,3,5-triazin-2-yl)-4-methylmorpholinium chloride) (69 mg; 1 eq) was added to the HA solution and allowed to react for 30 minutes, under stirring and at room temperature. Wulff-type phenylboronic acid (wPBA; 27.5 mg; 0.5 eq) was added to the activated HA solution and allowed to react for 3 days, under stirring and at room temperature. The solution was filter-sterilized and dialyzed against 1×PBS buffer (pH 7.4) for 1 day, then deionized water for 2 days (MWCO 12-14 kDa, Spectrum Labs). The solution was lyophilized and stored at 4° C. The degree of substitution was determined by $^1H$ NMR (400 MHz, $D_2O$, 6). A similar procedure was applied for the grafting of various aminated boronic acid derivatives (i.e., 2-aminophenylboronic acid, 3-aminophenylboronic acid, 4-aminophenylboronic acid, 5-aminobenzoxaborole) to various polysaccharides (i.e., 20/100/500 kDa hyaluronic acid, carboxymethylcellulose, alginate), adjusting the equivalents based on the solubilities of the reagents and the resulting modified polymers.

Synthesis of diol-modified polysaccharide. A typical synthesis was as follows: 500 kDa HA (100 mg) was dissolved in MES buffer pH 5.5 (10 mL). DMT-MM (137 mg; 2 eq) was added to the HA solution and allowed to react for 30 minutes, under stirring and at room temperature. Glucamine (90 mg; 1 eq) was added to the activated HA solution and allowed to react for 3 days, under stirring and at room temperature. The solution was filter-sterilized and dialyzed against 1×PBS buffer (pH 7.4) for 1 day, then deionized water for 2 days (MWCO 12-14 kDa, Spectrum Labs). The solution was lyophilized and stored at 4° C. The degree of substitution was determined either by elementary analysis (nitrogen/carbon ratio) of the purified product or by quantification of unreacted aminated molecules in the crude mixture using 2,4,6-Trinitrobenzene Sulfonic Acid (TNBSA) titration. A similar procedure was applied for the grafting of various diol-containing aminated molecules (i.e., glucamine, isoserinol, glucosamine, galactosamine, fructosamine, dopamine, 1-Amino-1-deoxy-D-galactitol, tris (hydroxyl-methyl)aminomethane) to various polysaccharides (i.e., 20/100/500 kDa hyaluronic acid, carboxymethylcellulose, alginate), adjusting the equivalents based on the solubilities of the reagents and the resulting modified polymers.

Synthesis of Wulff-type boronic acid-modified PEG. 4-arm PEG-$NH_2$ (MW=2 kDa; 2.418 g) was dissolved in methanol (24 mL). 2-formylaryl boronic acid (943 mg; 1.3 eq) was added to the PEG solution, and allowed to react overnight, under stirring and at room temperature. The solution was cooled on ice, and $NaBH_4$ (274 mg; 1.5 eq) was added to it, prior to stirring for 48 hours at room temperature. 20 mL of deionized water were added, and a liquid-liquid extraction was performed using dichloromethane (3×50 mL), before drying the organic phase with anhydrous $Na_2SO_4$. The solution was filtered and dialyzed against deionized water for 1 day (MWCO 1 kDa, Spectrum Labs). The solution was lyophilized and stored at 4° C. The degree of substitution was determined by $^1H$ NMR (400 MHz, $D_2O$, 6).

Synthesis of boronic acid-based polysaccharide hydrogel. A typical synthesis of a boronic acid hydrogel was, as follows: in a 2-mL Eppendorf tube, 10 mg of HA-wPBA were dissolved in PBS (1 mL), at room temperature for 1-2 hours. A similar procedure was used to dissolve 10 mg of HA-glucamine in PBS (1 mL). In a 2-mL Eppendorf tube, HA-wPBA and HA-glucamine solutions were rapidly mixed together in a 1:1 volume ratio, and the pipettable, dynamic hydrogel solution was used prior to gelation. Using a similar procedure, combinations of various phenylboronic acid-modified polysaccharides and diol-modified polysaccharides were tested. When necessary, a double-barrel syringe was used for convenience.

II. Physicochemical Properties

Swelling/Stability Tests. Hydrogels were prepared as described above. Aliquots (3×100 μL) of hydrogels were transferred in pre-weighed, 2-mL Eppendorf tubes, and left for equilibration at 37° C. for 30 minutes. The gel-containing tubes were weighed, and 900 μL of warm PBS (37° C.) was added to each. At specific time points, the supernatant was removed, the gel surface carefully dried with Kimwipes, and the tube weighed. The swelling was determined as the ratio of the hydrogel mass at a given time point divided by its initial mass.

Rheological Evaluation of Dynamic Hydrogels. Hydrogels were prepared as described above. Viscoelastic data were collected using a HAAKE MARS rheometer (Thermo Fisher Scientific, Germany), equipped with a 20 mm titanium cone (Ti 20 L; Thermo Fisher Scientific, Germany) for parallel plate measurements, and a Peltier plate for temperature control. A solvent trap was used to minimize evaporation during the measurements. To measure the shear storage modulus (G') and shear loss modulus (G") of gels, frequency sweeps (0.01-10 Hz) were performed, under a constant shear stress of 1 Pa and at 37° C. Self-healing properties were evaluated by measuring G' and G" over time at 1 Hz and 7° C., under alternated stress of 1 Pa for 100 s (non-destructive stress) and 500 Pa for 50 s (destructive stress).

III. Biological Properties

Hydrogel Component Cytocompatibility. HA-wPBA, PEG-wPBA and HA-glucamine solutions were separately tested for cytocompatibility, using L929 fibroblast cells as a model cell line. Polymer solutions (1%) were prepared under sterile conditions, using sterile polymers and cell medium (Dulbecco's modified Eagle medium (DMEM) supplemented with 10% fetal bovine serum and 1% penicillin/streptomycin). Cells were seeded in cell medium at 15,000 cells/well (100 μL) in standard polystyrene 96-well plates, and incubated (37° C., 5% $CO_2$, 95% humidity) overnight. The medium was replaced with 100 μL of 1% polymer solution prior to cell incubation. After specific incubation time periods (0, 24 hours and 48 hours), cells were tested for metabolic activity, using a CCK-8 assay kit and following supplier's protocol. CCK-8 medium was subsequently replaced with Tris/EDTA (TE) buffer before freezing cells (−80° C.) overnight. Cell proliferation was then assessed, using a Quant-iT™ PicoGreen™ assay kit for DNA quantification and following supplier's recommendations.

3D Cell Survival Evaluation. 1% HA-wPBA and 2% HA-glucamine solutions were prepared under sterile conditions, using cell medium (DMEM supplemented with 10% fetal bovine serum, 1% penicillin/streptomycin, and 1% amphotericine B). The 2% HA-glucamine solution was mixed with a solution of adipose-derived multipotent stromal cells (MSCs) of $8\times10^6$ cells/mL in a 1:1 ratio to yield a 1% HA-glucamine solution containing $4\times10^6$ cells/mL. 0.5 mL of 1% HA-wPBA solution was mixed with 0.5 mL of 1% HA-glucamine/cell solution, and 100 μL hydrogel (100 Kcells/well) were plated in a 96-well plate. The cell-containing hydrogels were incubated (37° C., 5% $CO_2$, 95% humidity) with 150 μL of cell medium on top, which was changed every other day, prior to analysis. A 2D control was performed, at a density of $5\times10^3$ cells per well, in 250 μL cell medium, with feeding every other day. After specific incubation time periods (0, 1 day and 7 days), cell viability was assessed by live/dead staining and confocal microscopy (Nikon A1), using Calcein AM (live cells, Sigma-Aldrich), ethidium homodimer (dead cells, Sigma-Aldrich) and Hoechst (all cell control, Invitrogen), as per the manufacturer's instructions. Average viability was obtained from 3 biological replicates.

IV. Results

The results obtained are presented in FIGS. 1 to 6.

As a proof of concept, the present Inventors first demonstrated the successful synthesis of dynamic covalent hydrogels upon mixing of Wulff-PBA-modified hyaluronic acid (HA-wPBA) with glucamine-modified hyaluronic acid (HA-glucamine). Using 1% (w/v) HA and a wPBA:glucamine ratio of 1:2, they observed a frequency-dependent crossover of the storage modulus (G') and loss modulus (G") by rheometry, which is characteristic feature of dynamic covalent hydrogels (FIG. 1).

The present Inventors further demonstrated the self-healing property of the newly designed hydrogels, inherent of dynamic covalent polymer networks. Qualitatively, two separate HA-based dynamic hydrogels put into contact with each other formed a single gel within minutes (FIG. 2A). At a constant frequency of 1 Hz, and under alternated low (1 Pa) and high (500 Pa) stress, a time sweep measurement showed repeated disruption of the gel (G'<G") under high shear followed by effective recovery of its initial mechanical properties (G'>G"), further confirming self-healing (FIG. 2B).

Figure 3:
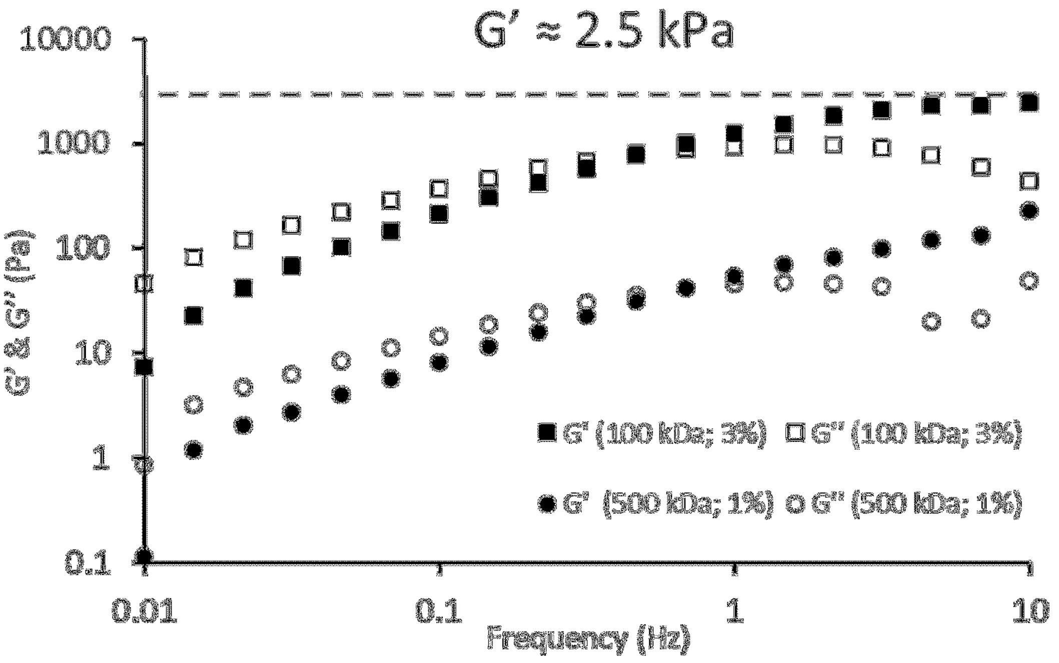
FIG. 3. Proof of concept of the tunability of the viscoelastic behavior of dynamic covalent gels, varying the molecule weight (100 kDa vs 500 kDa) and polymer content (1% vs 3% (w/v)) of hyaluronic acid-based dynamic covalent hydrogels. Storage stimulus (G') and loss modulus (G") were measured as a function of frequency.

The present Inventors then investigated the effect of the molecular weight and polymer content of these HA-based hydrogels on their viscoelastic behavior. Decreasing the molecular weight of the polymer precursors from 500 kDa to 100 kDa allowed them to increase the polymer content from 1% to 3% (w/v), ensuring workable viscosity of the precursor solutions and a broad range of crosslink density for the designed hydrogels. This allowed to obtain dynamic covalent hydrogels with shear storage modulus component (G') spanning orders of magnitude (from a few tens to a few thousands Pa), reflecting a variety of viscoelastic behaviors and high tunability of the system (FIG. 3).

Figure 4:
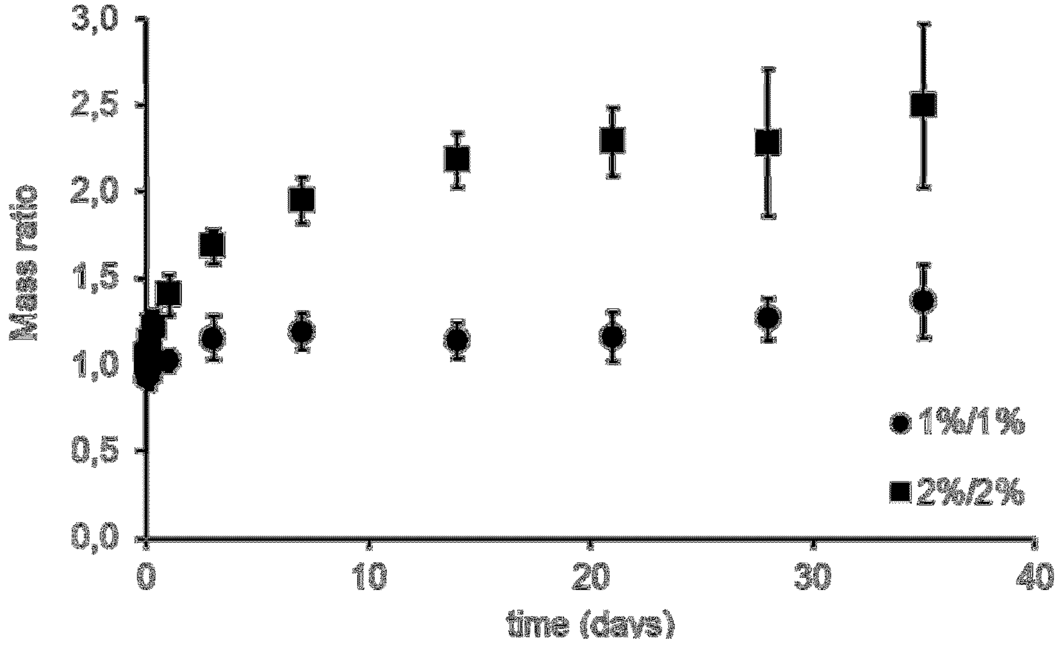
FIG. 4. Swelling/stability study of hyaluronic acid (HA)-based hydrogels, using HA-Wulff-PBA and HA-glucamine in a 1:1 volume ratio, at 1% vs 2% (w/v) polymer concentration. Tuning the polymer concentration of these gels allows to control their swelling and stability, with optimal formulations showing minimal swelling and stabilization within 3 days, followed by long-term stability (at least one month).
Figure 5:
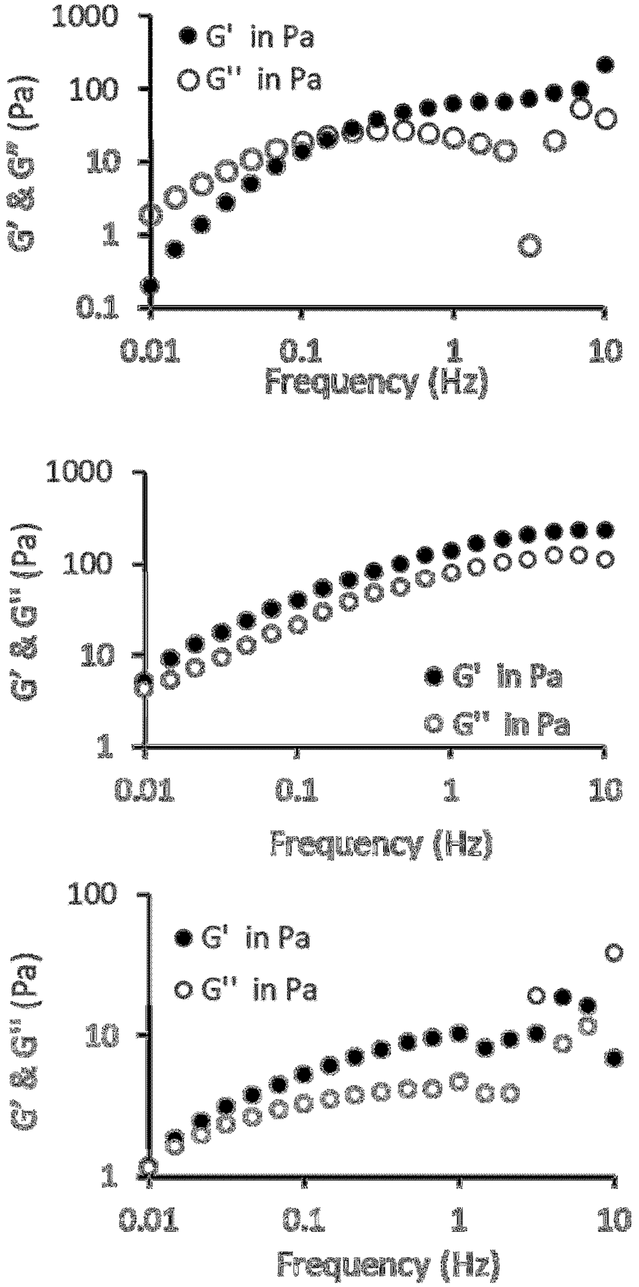
FIG. 5. Proof of concept of dynamic covalent hydrogels obtained from a variety of natural and synthetic polymers modified with either Wulff-PBA or glucamine. Storage modulus (G') and loss modulus (G") of (A) 1% (w/v) poly(ethylene glycol) (PEG)-Wulff-PBA mixed with 1% (w/v) HA-glucamine in a 1:1 volume ratio, (B) 1% (w/v) alginate-Wulff-PBA mixed with 1% (w/v) alginate-glucamine in a 1:1 volume ratio, and (C) 1% (w/v) carboxymethylcellulose-Wulff-PBA mixed with 1% (w/v) carboxymethylcellulose-glucamine in a 1:1 volume ratio, measured as a function of frequency.
Figure 6:
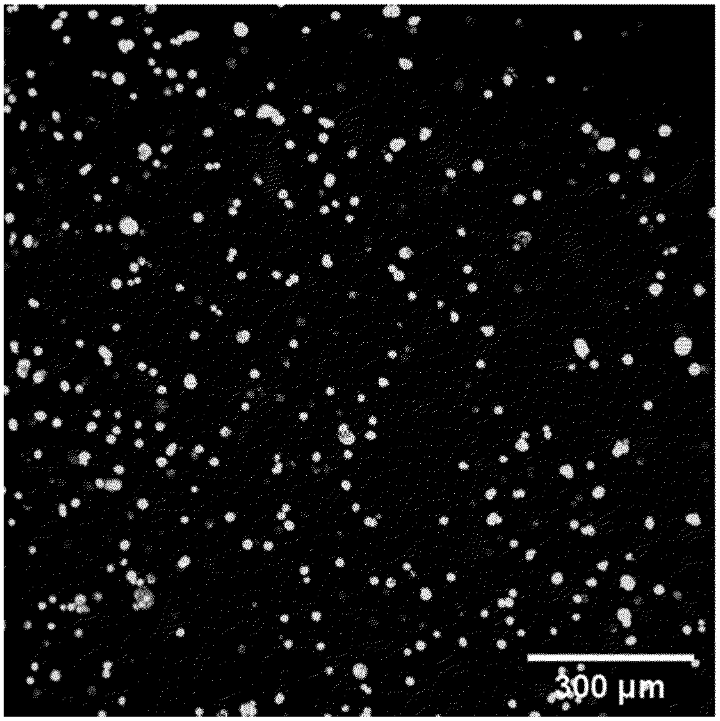
FIG. 6. Evaluation of adipose-derived multipotent stromal cell survival encapsulated in a typically dynamic covalent hydrogel (1% (w/v) HA-Wulff-PBA mixed with 1% (w/v) HA-glucamine in a 1:1 volume ratio), using confocal microscopy and live/dead staining.
Figure 6:
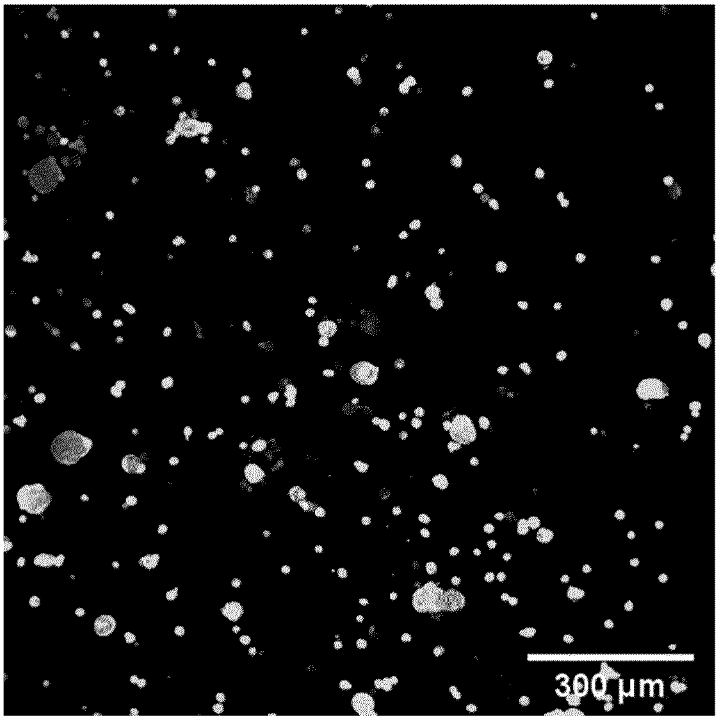

Using the newly discovered crosslinking pair (i.e., wPBA and glucamine), the swelling and stability of HA-based dynamic covalent hydrogels was evaluated. Comparing 1% and 2% (w/v) polymer content, the Inventors showed that optimal formulations of these new hydrogels lead to minimal swelling and long-term stability (at least one month), despite the reversible crosslinks of the polymer network (FIG. 4). This will further allow tuning of the swelling and stability properties of these dynamic hydrogels for various applications.

As a proof of concept of its versatility, the new crosslinking pair was applied to a variety of polymers. Dynamic covalent hydrogels were successfully obtained upon mixture of: 1% (w/v) poly(ethylene glycol) (PEG)-wPBA with 1% (w/v) HA-glutamined in a 1:1 volume ratio (FIG. 5A); 1% (w/v) alginate-wPBA with 1% alginate-glucamine in a 1:1 volume ratio (FIG. 5B); and 1% (w/v) carboxymethylcellulose-wPBA with 1% (w/v) carboxymethylcellulose-glucamine in a 1:1 volume ratio (FIG. 5C). Taken together, these results suggest that the new crosslink pair can be applied to synthetic and natural polymers, with different molecular weights, ionic strengths, and degradability properties.

Finally, the present Inventors have evaluated the cytocompatibility of HA-HA and HA-PEG dynamic covalent gels, assessing the survival (live/dead assay) of encapsulated adipose-derived multipotent stromal cells (A-MSCs) after 7 days of 3D culture by confocal microscopy. These results revealed the excellent survival (>90%) of A-MSCs encapsulated in these gels.

Example 2

Example 2 reports data on the physicochemical and biological properties of different boronic acid-diol couples according to the present invention for dynamic hydrogel design.

I. Comparison of Rheological Properties of Different Boronic Acid-Diol Couples Immobilized on Polymers The Inventors sought to identify new boronic acid-diol couples with an affinity high enough to form dynamic covalent hydrogels when immobilized on polymers, under physiological conditions of pH and temperature.

Hyaluronic acid (HA) was selected as polymer backbone because it is often considered as a polymer of choice for biomedical applications. Using DMT-MM as an activating agent (see Example 1), different aminated phenyl boronic acid (PBA) derivatives were each immobilized onto HA via amidation. Following a similar procedure, a series of diol-containing molecules were grafted onto HA. To be able to compare the various boronic acid-diol couples, reaction conditions were adjusted to match the degrees of substitution of the various PBAs 20-25%) and diols 30-35%). Interestingly, 2-amino-phenyl boronic acid (2PBA), 3-amino-phenyl boronic acid (3PBA), 4-amino-phenyl boronic acid (4PBA) and amino-benzoxaborole (BX) all required the use of a small volume of DMSO to reach degrees of substitution of 20-25%; and 3PBA-modified HA precipitated during the synthesis. In contrast, Wulff-type phenyl boronic acid (wPBA), because of its positively charge character, could be immobilized under aqueous conditions (i.e., without the use of DMSO) up to a degree of substitution of at least 40%.

Figure 7:
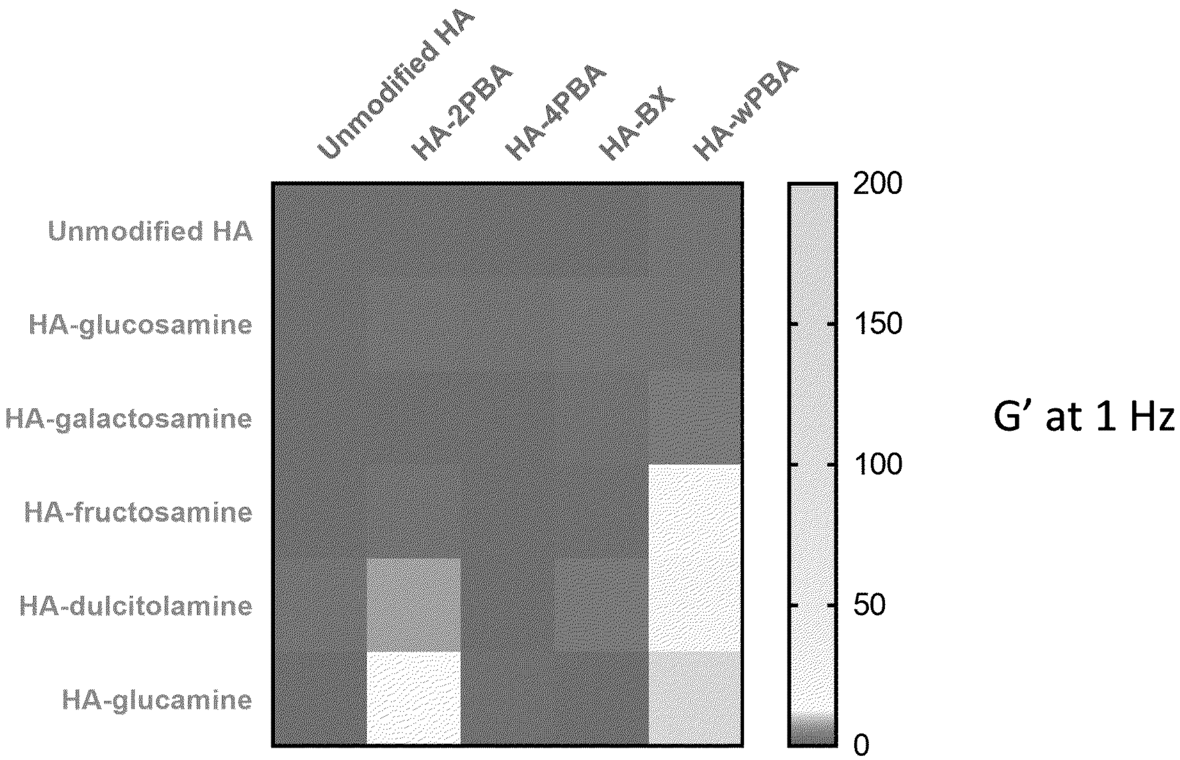
FIG. 7. Comparison of the rheological properties (frequency sweeps; G', shear elastic modulus) of different boronic acid-diol couples immobilized on hyaluronic acid (HA) under physiological conditions of pH and temperature (See Example 2, paragraph I).

All the boronic acid-diol couples were then tested by mixing, two by two, all the PBA-modified and diol-modified HA components. The rheological measurements obtained (frequency sweeps; G', shear elastic modulus) are reported in FIG. 7. They revealed a series of couples capable of forming hydrogels under physiological conditions (e.g., HA-glucamine and HA-wPBA; HA-fructosamine and HA-wPBA; HA-dulcitolamine and HA-wPBA; HA-glucamine and HA-2PBA and HA-dulcitolamine and HA-2PBA). In particular, the association of HA-glucamine and HA-wPBA led to the formation of viscoelastic materials with an elastic component one to several orders of magnitude higher than any of the other couples. Interestingly, the BX-modified polymer, which was reported to favor hydrogel formation more easily in the presence of diols because of its chemical structure, did not lead to any remarkable gelation properties.

II. Optimized Formulations of HA-wPBA-HA-Glucamine Gels with Improved Physicochemical (Viscoelastic) Properties In order to tune the viscoelastic behavior of the gels made of HA-wPBA and HA-glucamine, the Inventors screened a large panel of compositions, varying the molecular weight of the polymer hyaluronic acid (HA), the total concentration of HA, the degrees of substitution of each of the two components (HA-wPBA and HA-glucamine), and the wPBA:glucamine molar ratio.

Figure 8:
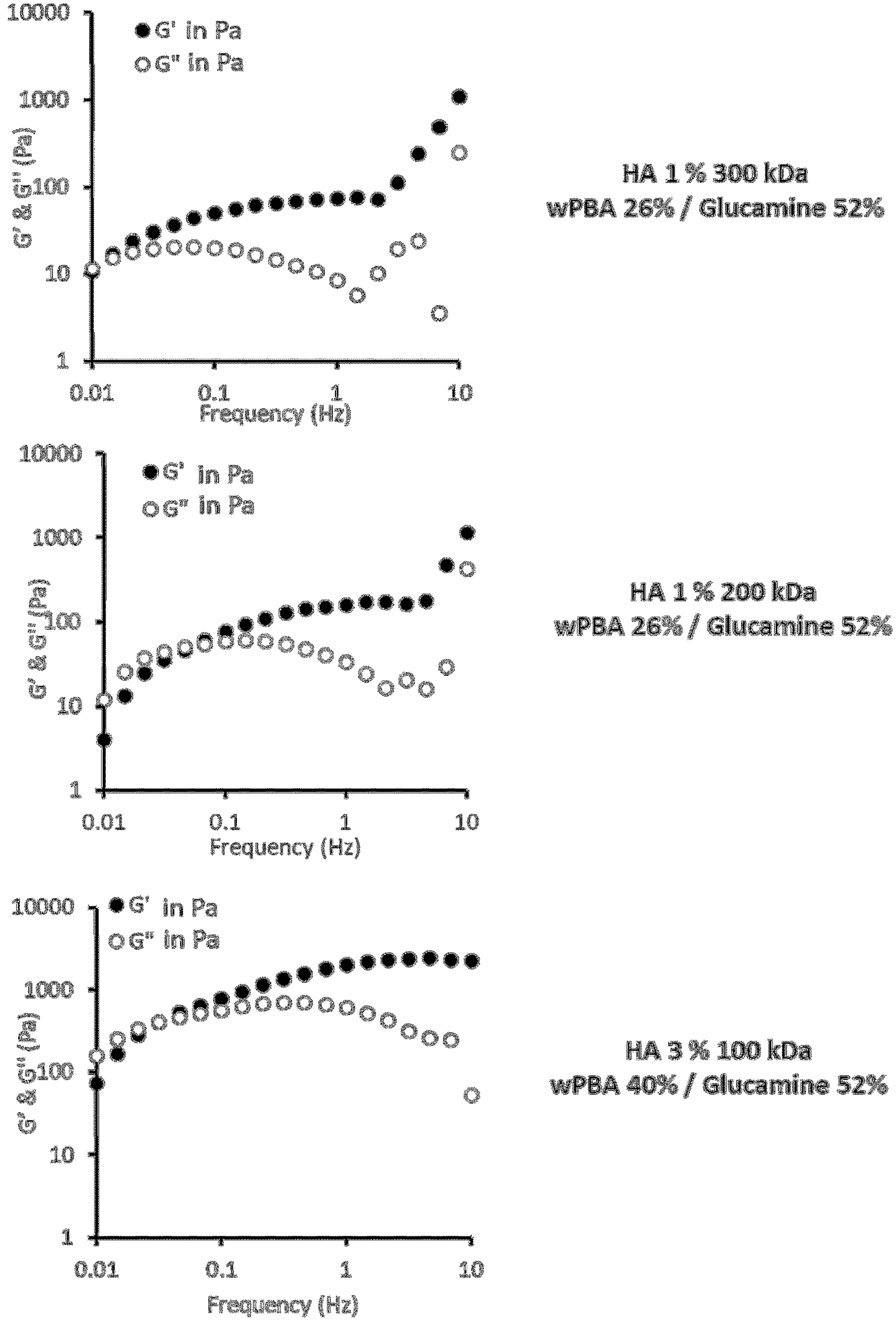
FIG. 8. Storage modulus (G') and loss modulus (G") of three specific optimized formulations of dynamic covalent hydrogels of HA-Wulff-PBA and HA-glucamine showing various viscoelastic profiles. HA polymers with different molecular weights (300 kDa, 200 kDa or 100 kA), different total concentrations of HA (1% or 3% w/v), different degrees of substitution for the two components (HA-wPBA—26% or 40%; HA-glucamine—52%) were used, while the molar ratio wPBA:glucamine was kept constant at 1:1. (See Example 2, paragraph II)

Several compositions of interest were identified, exhibiting specific viscoelastic behavior, as observed via rheological measurements (in a frequency sweep test, the G'/G" crossover of a dynamic gel is directly related to its relaxation time). FIG. 8 shows three of such specific optimized compositions: in the first one, the total concentration of HA is 1%, the molecular weight of HA is 300 kDA, the degree of substitution of HA-wPBA is 26% and the degree of substitution of HA-glucamine is 52%; in the second one, the total concentration of HA is 1%, the molecular weight of HA is 200 kDa, the degree of substitution of HA-wPBA is 26% and the degree of substitution of HA-glucamine is 52%; and in the third one, the total concentration of HA is 3%, the molecular weight of HA is 100 kDA, the degree of substitution of HA-wPBA is 40% and the degree of substitution of HA-glucamine is 52%. In each of the three specific compositions, the wPBA:glucamine molar ratio is 1:1.

Figure 9:
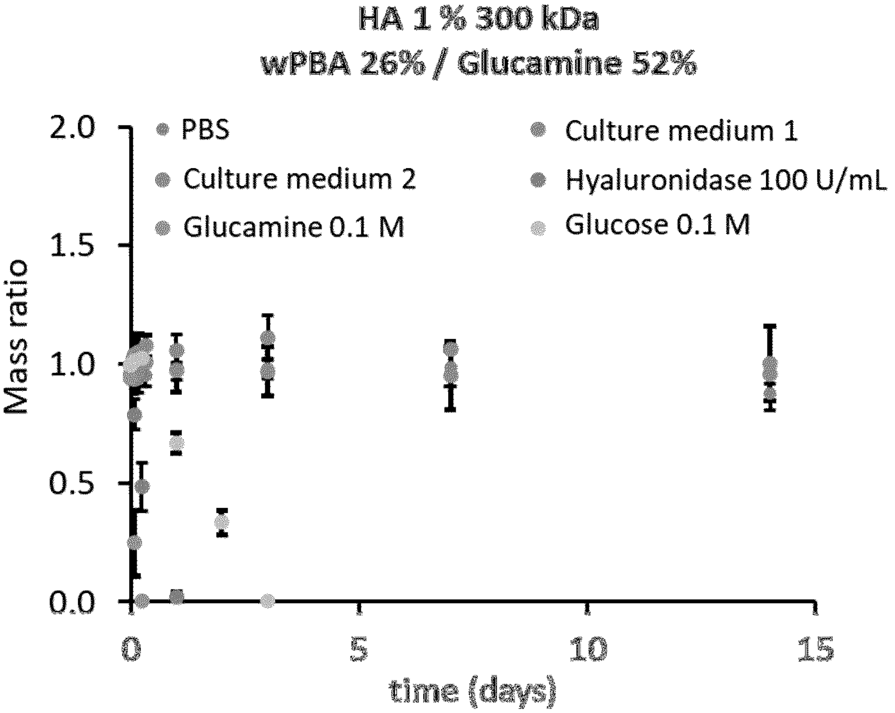
FIG. 9. Design of minimally- to non-shrinking/non-swelling boronic acid-based hydrogels. The variations of hydrogel mass ratio as a function of time are reported (A) for a dynamic covalent hydrogel of HA-Wulff-PBA and HA-glucamine, where a 300 kDa HA polymer was present at a total concentration of 1% w/v, the degree of substitution of HA-wPBA was 26%, the degree of substitution of HA-glucamine was 52%, and the molar ratio wPBA:glucamine was 1:1; and (B) for an identical dynamic covalent hydrogel of HA-Wulff-PBA and HA-glucamine, except that the HA polymer had a molecular weight of 200 kDa. The variations of the hydrogel mass ratio as a function of time were studied in PBS (A and B), in two different culture media (A) and in the presence of glucose, of glucamine and of hyaluronidase (A). (See Example 2, paragraph II)
Figure 9:
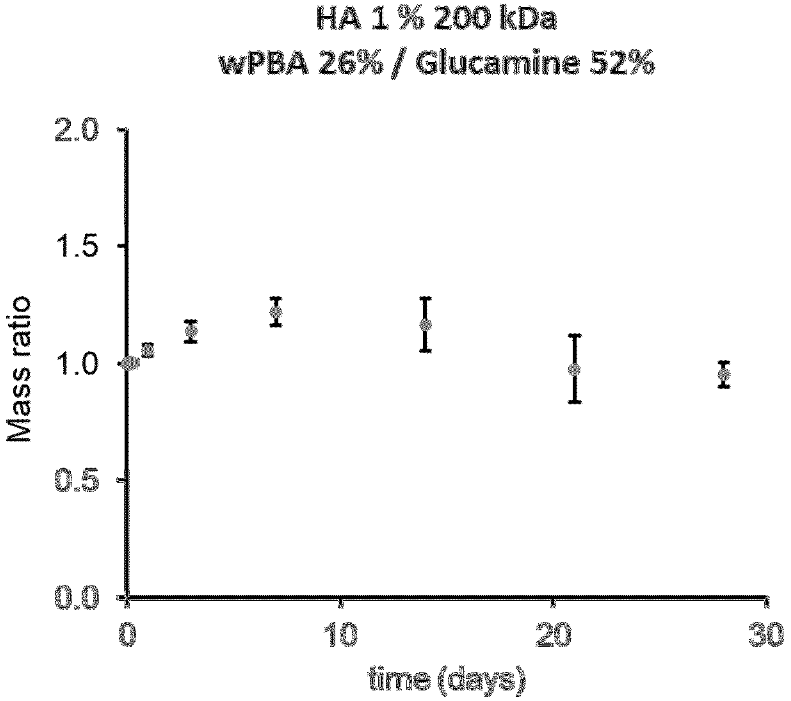

More importantly, while boronic acid-based hydrogels tend to shrink, the present Inventors were able to design minimally- to non-shrinking/non-swelling boronic acid-based hydrogels by carefully balancing the shrinking tendency of the network with the swelling tendency of HA, which is a charged and hydrophilic polymer (see FIG. 9(B) and FIG. 9(A) curves in PBS, Culture Medium 1 and Culture Medium 2). The optimal formulations were also stable for weeks to months under physiological conditions of pH and temperature, which was never reported for boronic acid-based hydrogels to date. Owing to the dynamic character of their networks, the new gels could easily be dissolved by simply adding a competing, free diol-containing molecule, such as glucose or glucamine (see FIG. 9(A)). The HA-based gels could also be enzymatically degraded using hyaluronidase, together making the dynamic covalent hydrogels of the invention sugar-responsive and biodegradable (see FIG. 9(A)).

III. Cytocompatibility of Boronate Ester Hydrogels

To validate the use of the new gels for biomedical applications, the cytocompatibility of boronate ester hydrogels of the invention with encapsulated cells was evaluated using a model cell line (L929 murine fibroblast cells). The gel used in the experiments reported in FIG. 6 was a hydrogel of HA-Wulff-PBA and HA-glucamine, where the total concentration of the 300 KDa HA polymer was 1% w/v, the molar ratio of boro:diol was 1:1, the degree of substitution of the HA-Wulff-PBA was 26% and the degree of substitution of the HA-glucamine was 52%. The cytocompatibility was assessed via cell viability (live/dead cell imaging), metabolic activity (CCK-8) and proliferation (PicoGreen) assays.

Figure 10:
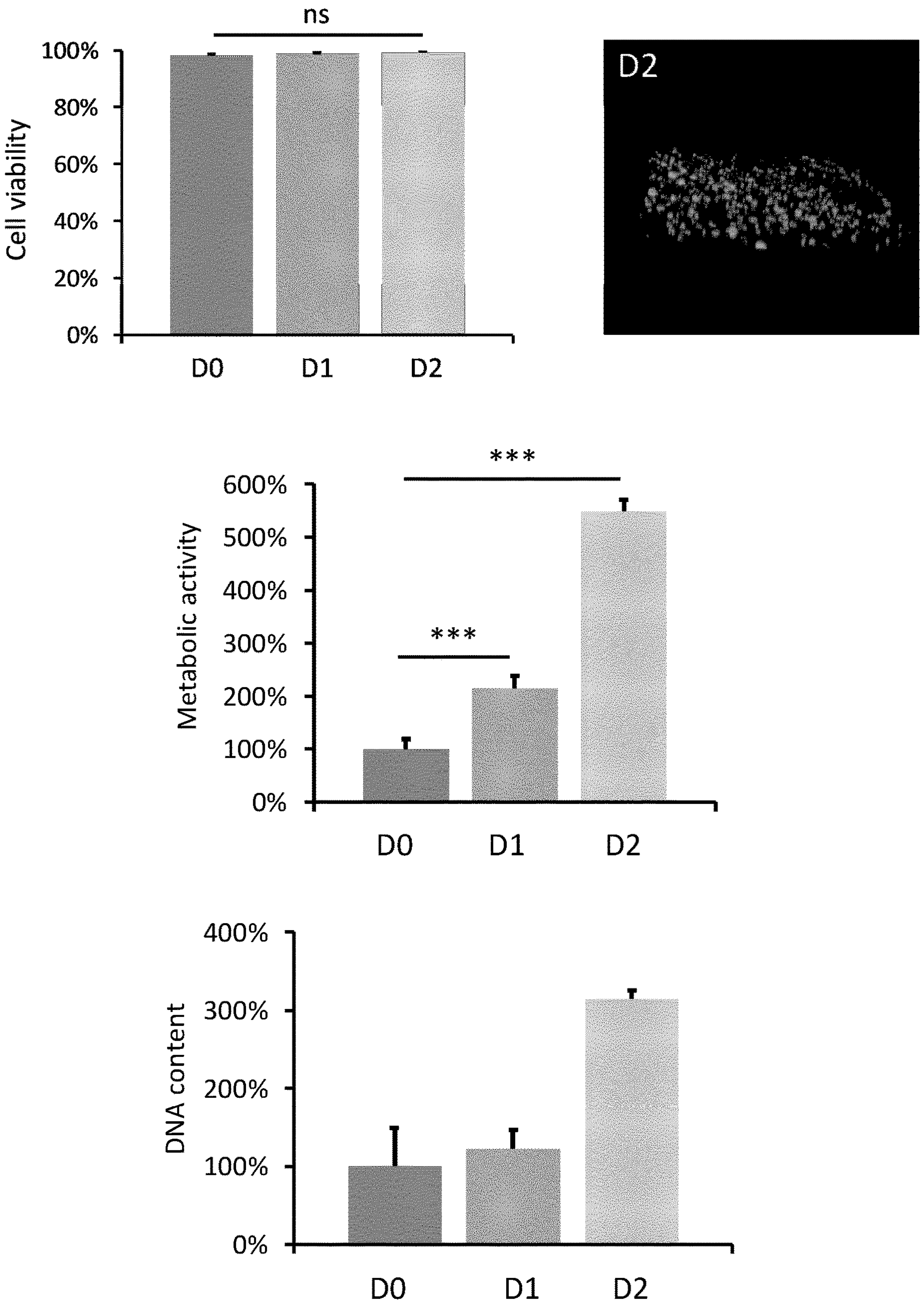
FIG. 10. Cytocompatibility of a boronic ester gel. Murine fibroblast cells (L929 cell line) were encapsulated in a boronate ester hydrogel according to the invention (300 kDa HA; [HA]=1% w/v; Wulff-PBA substitution=26%; glucamine-substitution=52%:Wulff-PBA:glucamine ratio=1:1), and the cytocompatibility was assessed via cell viability (live/dead cell imaging), metabolic activity (CCK-8) and proliferation (PicoGreen) assays. The results are reported for Days 0, 1 and 2 following cell encapsulation in the hydrogels. The image on the right of the cell viability graph is a representative image of the high cell viability (>98%) observed after 2 days of 3D cell culture. (See Example 2, paragraph III)

The results obtained are reported on FIG. 10. After two days, the collected data show high cell viability, accompanied with increased metabolic activity and cell number, together indicating the excellent cytocompatibility of the tested gel. Similar results with obtained with different other hydrogels according to the present invention.

IV. Optimized Boronic Acid Hydrogels are Printable

Figure 11:
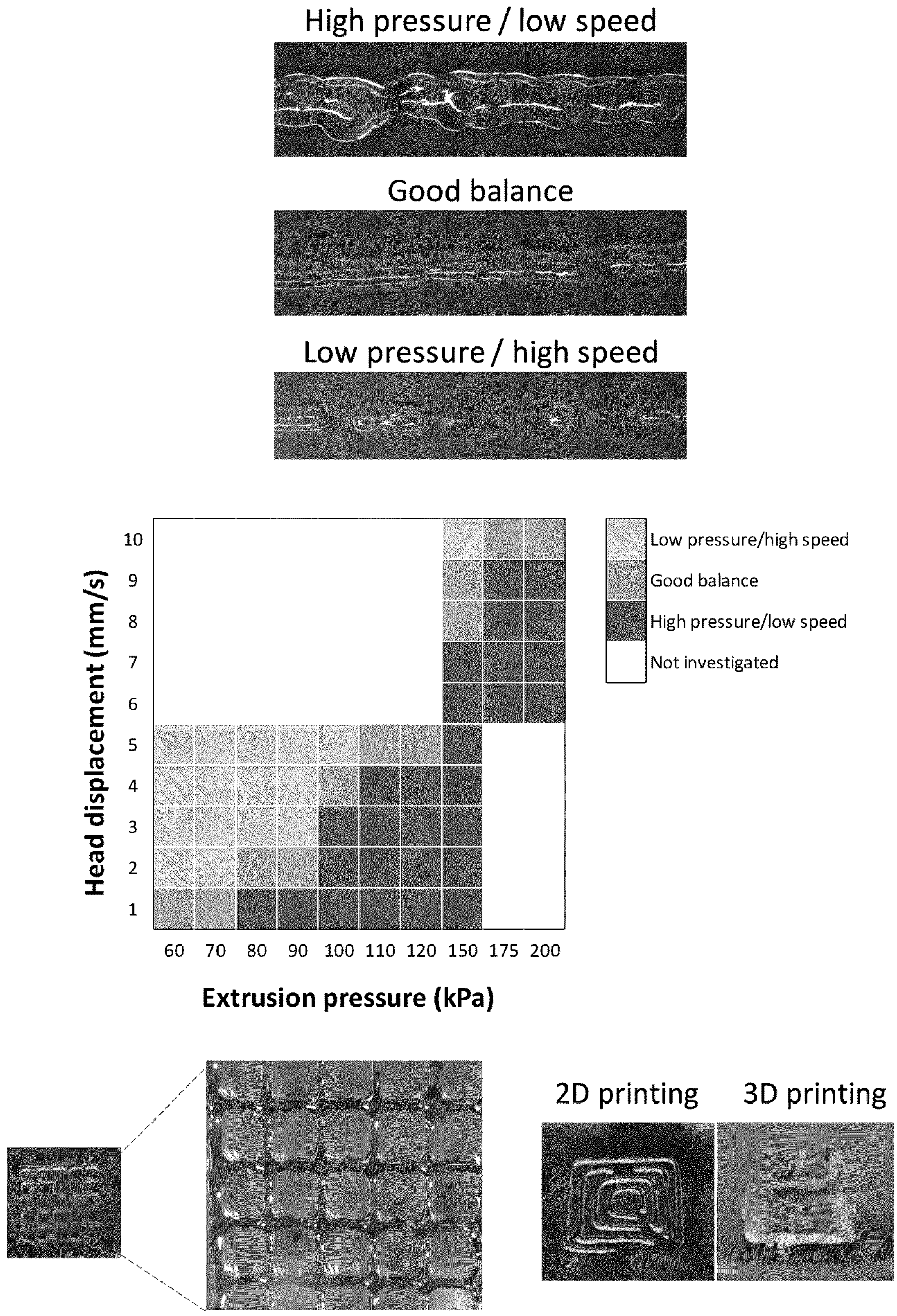
FIG. 11. Optimized Dynamic Covalent Hydrogels are Printable. The top three images show how a good balance of extrusion pressure and speed allows the printing of a continuous and well-resolved filament of boronic ester hydrogels. The middle graph highlights in green the large range of extrusion/pressure couple that can be used to successfully print boronic ester hydrogels of the present invention, while showing conditions leading to broken filaments in yellow, and conditions leading to poorly resolved filament in red. The bottom images are exempled of successfully printed shapes, from one and multiple layers of gels. (See Example 2, paragraph IV)

Since dynamic covalent hydrogels according to the present invention have the particularity to temporarily flow under shear (see Example 1), the Inventors envisioned the use of the new hydrogels for the development of innovative bioinks in the context of bioprinting. The preliminary data are presented on FIG. 11. The following composition was used as a typical example: 200 kDa HA, total concentration of HA=1% w/v, degree of substitution of HA-Wulff-PBA: 26%, degree of substitution of HA-glucamine=52%, molar ration Wulff-PBA:glucamine=1:1. The results obtained show that optimized formulations of the new hydrogels, associated with optimal printing conditions (e.g., head displacement, extrusion pressure), can be easily printed, with good shape fidelity.

V. Combination with Other Crosslinking Mechanisms

To enlarge the scope of biomedical applications of the new hydrogels, the present Inventors sought to demonstrate the feasibility of associating the discovered crosslinking mechanism with other chemical reactions, in particular the "Click" and bioorthogonal chemical reactions.

Figure 12:
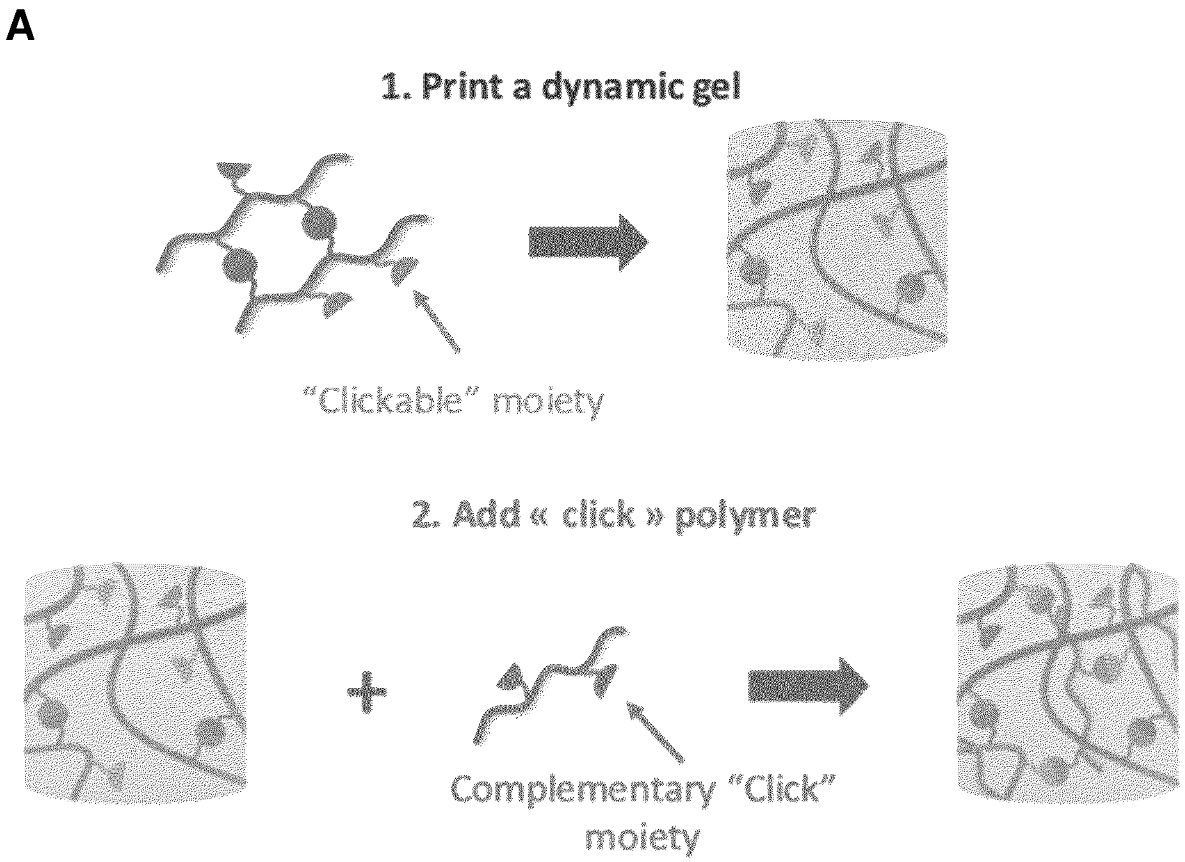
FIG. 12. Combination of the Crosslinking Mechanism of the Invention with the "Click" Chemical Reaction. (A) The scheme highlights the potential combination of the crosslinking mechanism with a "Click" chemical reaction to tune the composition and physicochemical properties of the obtained gel. In the particular context of bioprinting, such a strategy can be used to mechanically reinforce a construct post-printing. (B) is a graph showing the successful mechanical reinforcement of a construct post-printing upon immersion in a medium containing the appropriate "clikable" polymer. In this example, the strain-promoted azide-alkyne cycloaddition (SPAAC) between bicyclonyne (BCN) and azide ($N_3$) was used as a model "click" reaction. The boronate ester gel was chemically modified with BCN, allowing the post-printing modification with azide-modified hyaluronan (100 kDa). (See Example 2, paragraph V).
Figure 12:
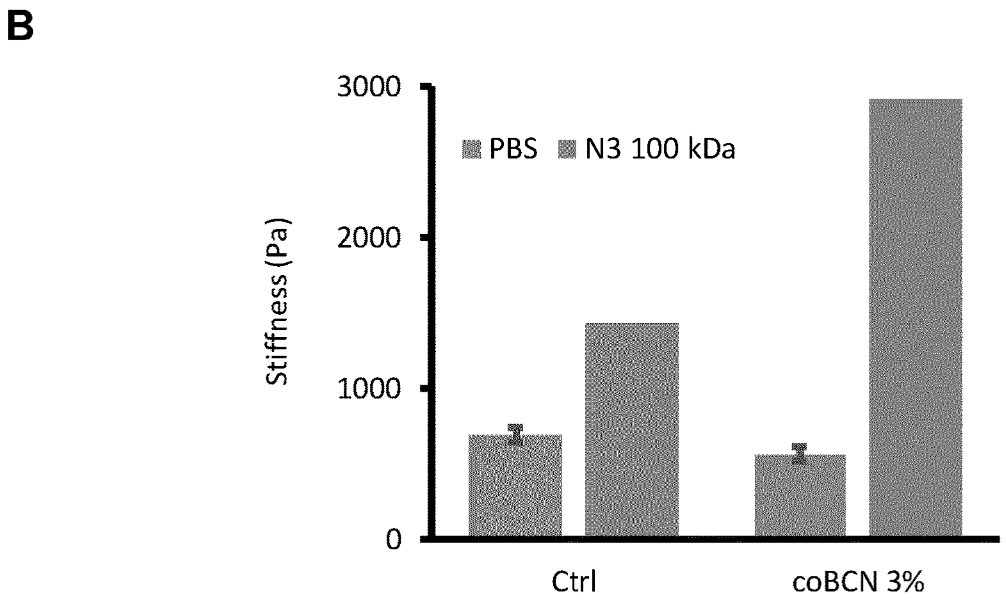

As preliminary data, it is shown that a clickable moiety can be co-immobilized onto one of the two polymer components of the hydrogel, allowing to tune the physicochemical properties of the gel, in time and space (see FIG. 12(A)). For example, the co-crosslinking of boronic acid-based hydrogels can be used to stabilize and/or mechanically reinforce a bioprinted construct post-printing. The strain-promoted azide-alkyne cycloaddition (SPAAC) between bicyclonyne (BCN) and azide (N3) was used as a model "click" reaction. A 200 kDa boronate ester gel (total concentration of HA=1%; Wulff-PBA substitution=16%; glucamine substitution=52%; molar Wulff-PBA:glucamine ratio=1:1) was chemically modified with BCN (4% substitution as a co-substituent on HA-glucamine), allowing the post-printing modification with azide-modified hyaluronan (100 kDa; HA-$N_3$). By immersing the bioprinted boronate ester gel overnight in PBS containing 0.5% HA-$N_3$, the stiffness of the gel increased from 600 Pa to 3000 Pa.

This strategy can be used for the immobilization of molecules of interest (e.g., peptides, growth factors, drugs, fluorophores), the development of evolutive 3D culture system with cell-material interactions adjusted in time and space, and more.

What is claimed is:

1. A crosslinking pair of hydrogel precursor polymers comprising:

(1) a first hydrogel precursor polymer consisting of a first polymer modified with a Wulff-type phenylboronic acid, and (2) a second hydrogel precursor polymer consisting of a second polymer modified with glucamine.

2. The crosslinking pair of hydrogel precursor polymers according to claim 1, wherein the first polymer is grafted with the Wulff-type phenylboronic acid and the second polymer is grafted with glucamine.

3. The crosslinking pair of hydrogel precursor polymers according to claim 1, wherein the first and second polymers are independently selected from natural polymers, semi-synthetic polymers, and synthetic polymers.

4. The crosslinking pair of hydrogel precursor polymers according to claim 3, wherein at least one of the first and second polymers is selected from biocompatible, biodegradable, hydrophilic natural polymers, semi-synthetic polymers, and synthetic polymers.

5. The crosslinking pair of hydrogel precursor polymers according to claim 1, wherein the first hydrogel precursor polymer or the second hydrogel precursor polymer is directly or indirectly covalently linked to a bioorthogonal functional moiety or to a clickable moiety.

6. The crosslinking pair of hydrogel precursor polymers according to claim 1, wherein the first hydrogel precursor polymer is in a first aqueous solution; and the second hydrogel precursor polymer is in a second aqueous solution, the first and second aqueous solutions being separate aqueous solutions.

7. The crosslinking pair of hydrogel precursor polymers according to claim 6, wherein at least one of the first and second aqueous solutions comprises a component selected from the group consisting of cells, bioactive agents, visualization agents, and any combination thereof.

8. A dynamic covalent hydrogel composed of a first hydrogel precursor polymer and a second hydrogel precursor polymer of a crosslinking pair as defined in claim 1, wherein the first and second hydrogel precursors are crosslinked by dynamic covalent bonds.

9. A dynamic covalent hydrogel according to claim 8 further comprising a component selected from the group consisting of cells, bioactive agents, visualization agents, and any combination thereof.

10. A pharmaceutical composition comprising a crosslinking pair of hydrogel precursor polymers according to claim 1, and at least one pharmaceutically acceptable carrier or excipient.

11. A pharmaceutical composition comprising a dynamic covalent hydrogel according to claim 8, and at least one pharmaceutically acceptable carrier or excipient.

12. The pharmaceutical composition according to claim 10, wherein the first hydrogel precursor polymer and the second precursor hydrogel polymer are contained in a multi-barrel syringe.

13. A kit comprising a crosslinking pair of hydrogel precursor polymers according to claim 1, and instructions to use the crosslinking pair.

14. A kit comprising a dynamic covalent hydrogel according to claim 8, and instructions to use the dynamic covalent hydrogel.

15. A kit comprising a pharmaceutical composition according to claim 10, and instructions to use the pharmaceutical composition.

16. A method for preparing a dynamic covalent hydrogel comprising a step of mixing a first hydrogel precursor polymer and a second hydrogel precursor polymer of a crosslinking pair as defined in claim 1 to obtain a dynamic covalent hydrogel.

17. A method according to claim 16, wherein said method is carried out under physiological conditions.

18. The crosslinking pair of hydrogel precursor polymers according to claim 1, wherein the Wulff-type phenylboronic acid has formula (II):

(II)

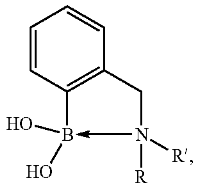

wherein R and R' are independently selected from hydrogen, substituted or unsubstituted $C_1$-$C_{20}$ alkyls, substituted or unsubstituted $C_1$-$C_{10}$ alkenyls, substituted or unsubstituted $C_1$-$C_{10}$ alkynyls, acyls-C(═O) $R_{1a}$, wherein $R_{1a}$ is a substituted or unsubstituted $C_1$-$C_{20}$ alkyl group) and carboxy groups-C(═O) $OR_{1b}$, wherein $R_{1b}$ is a substituted or unsubstituted $C_1$-$C_{20}$ alkyl group, wherein substituted alkyls, alkenyls and alkynyls are substituted with one or more substituents selected from halogen (F, Br, I, Cl), hydroxy (—OH), amino (—$NR_2R_3$, wherein $R_2$ and $R_3$ are independently selected from hydrogen and substituted or unsubstituted $C_1$-$C_{20}$ alkyl), alkoxy (—$OR_{1c}$, wherein Ric is a substituted or unsubstituted $C_1$-$C_{20}$ alkyl group), carboxy (—C(═O) $OR_{1b}$, wherein $R_{1b}$ is a substituted or unsubstituted $C_1$-$C_{20}$ alkyl group), amido (—$NR_2$C(═O) $R_3$ or —C(═O) $NR_2R_3$, wherein $R_2$ and $R_3$ are independently selected from hydrogen and substituted or unsubstituted $C_1$-$C_{20}$ alkyl), nitro (—$NO_2$), oxo (═O), and cyano (—CN) groups.

19. The crosslinking pair of hydrogel precursor polymers according to claim 18, wherein the Wulff-type phenylboronic acid is 2-((dimethylamino) methyl)-phenylboronic acid.

20. The crosslinking pair of hydrogel precursor polymers according to claim 18, wherein the Wulff-type phenylboronic acid is (2-(((4-aminobutyl) amino)-methyl) phenyl) boronic acid.

21. A method for delivering cells and/or bioactive agents to a subject, said method comprising a step of using a crosslinking pair of hydrogel precursor polymers according to claim 1 for delivering said cells and/or bioactive agent to said subject.

22. A method of viscosupplementation in a subject, said method comprising a step of injecting a crosslinking pair of hydrogel precursor polymers according to claim 1 in at least one joint in said subject.

23. A method of regenerative medicine in a subject, said method comprising steps of (a) using a crosslinking pair of hydrogel precursor polymers according to claim 1 to produce a tissue equivalent and (b) implanting the tissue equivalent obtained in step (a) into said subject.

* * * * *